(12) United States Patent
Ouellet et al.

(10) Patent No.: US 6,515,204 B1
(45) Date of Patent: Feb. 4, 2003

(54) CORN SILK GENE AND REGULATORY REGION

(75) Inventors: Thérèse Ouellet, Nepean (CA); Jas Singh, Nepean (CA); Titus Tao, Ottawa (CA); John Simmonds, Nepean (CA)

(73) Assignee: Her Majesty the Queen in right of Canada, as represented by The Minister of Agriculture and Agri-Food, Ottawa (CA)

( * ) Notice: Subject to any disclaimer, the term of this patent is extended or adjusted under 35 U.S.C. 154(b) by 0 days.

(21) Appl. No.: 09/680,175

(22) Filed: Oct. 5, 2000

Related U.S. Application Data

(63) Continuation-in-part of application No. 09/412,704, filed on Oct. 5, 1999, now abandoned.

(51) Int. Cl.$^7$ ................................................. A01H 1/00
(52) U.S. Cl. ..................... 800/287; 435/69.1; 435/419; 536/24.1
(58) Field of Search .............................. 435/69.1, 320.1, 435/410, 419, 468; 536/24.1; 800/287, 300.1

(56) References Cited

U.S. PATENT DOCUMENTS

| | | | |
|---|---|---|---|
| 5,364,780 A | 11/1994 | Hershey et al. | 800/294 |
| 5,484,905 A | 1/1996 | Nasrallah et al. | 536/23.6 |
| 5,585,543 A | 12/1996 | Kao | 800/286 |
| 5,589,610 A | 12/1996 | De Beuckeleer et al. | 800/303 |
| 5,608,143 A | 3/1997 | Hershey et al. | 800/298 |
| 5,633,441 A | 5/1997 | De Greef et al. | 800/271 |
| 5,670,349 A | 9/1997 | Cramer et al | 435/69.1 |
| 5,723,763 A | 3/1998 | Mariani et al. | 800/306 |
| 5,767,374 A | 6/1998 | De Greef et al. | 800/267 |
| 5,859,351 A | 1/1999 | Staskawicz et al. | 800/301 |
| 5,907,083 A | 5/1999 | Robert et al. | 800/287 |

FOREIGN PATENT DOCUMENTS

| | | |
|---|---|---|
| WO | WO 94/25613 | 11/1994 |
| WO | WO 98/18939 | 5/1998 |
| WO | WO-98/39462 | * 9/1998 |
| WO | WO 99/02655 | 1/1999 |

OTHER PUBLICATIONS

Callie "Controlling gene expression in transgenics" Current Opinion in Plant Biology(1998)1:66–172.*
Kim et al. "Genomic organization and promoter activity of the maize starch, branching enzyme I gene" Gene (1998)216:233–243.*
Atkinson, et al., "Proteinase Inhibitors in *Nicotiana alata* Stigmas Are Derived from a Precursor Protein Which is Processed into Five Homologous Inhibitors," *The Plant Cell* 5:203–313 (1993).
Dzeizkalns, et al., "Distinct cis–Acting Elements Direct Pistil–Specific and Pollen–Specific Activity of the *Brassica S Locus Glycoprotein* Gene Promoter," *The Plant Cell* 5:855–863 (1993).
Goring, et al., "An S Receptor Kinase Gene in Self–Compatible *Brassica napus* Has a 1–bp Deletion," *The Plant Cell* 5:531–539 (1993).
Leung, David W., "Involvement of Plant Chitinase in Sexual Reproduction of Higher Plants," *Phytochemistry* 31:1899–1900 (1992).
Mirabella, et al., "The soybean ENOD40(2) promoter is active in *Arabidopsis thaliana* and is temporally and spatially regulated," *Plant Molecular Biology* 39:177–181.
Nasrallah et al, "Pollen–Stigma Signaling in the Sporophytic Self–Incompatibility Response," *The Plant Cell* 5:1325–1335 (1993).
Trick et al., "Sporophytic Self–Incompatibility Systems: *Brassica S Gene* Family," *International Review of Cytology* 140:185–524 (1992).

* cited by examiner

*Primary Examiner*—Remy Yucel
*Assistant Examiner*—Bronwen M. Loeb
(74) *Attorney, Agent, or Firm*—Quarles & Brady LLP

(57) ABSTRACT

The invention can be summarized as follows. Several silk-specific genes were isolated from corn silk. The specificity of their expression was determined by Northern analysis. A regulatory region was obtained from the silk gene, C3, and found to direct silk, and pistil, expression in transient assays and transgenic plants, in both monocot and dicot plants. The regulatory region of a silk gene may be used to drive the expression of a gene of interest within pistil or silk-tissues for a range of utilities including pathogen resistance or female sterility.

24 Claims, 12 Drawing Sheets

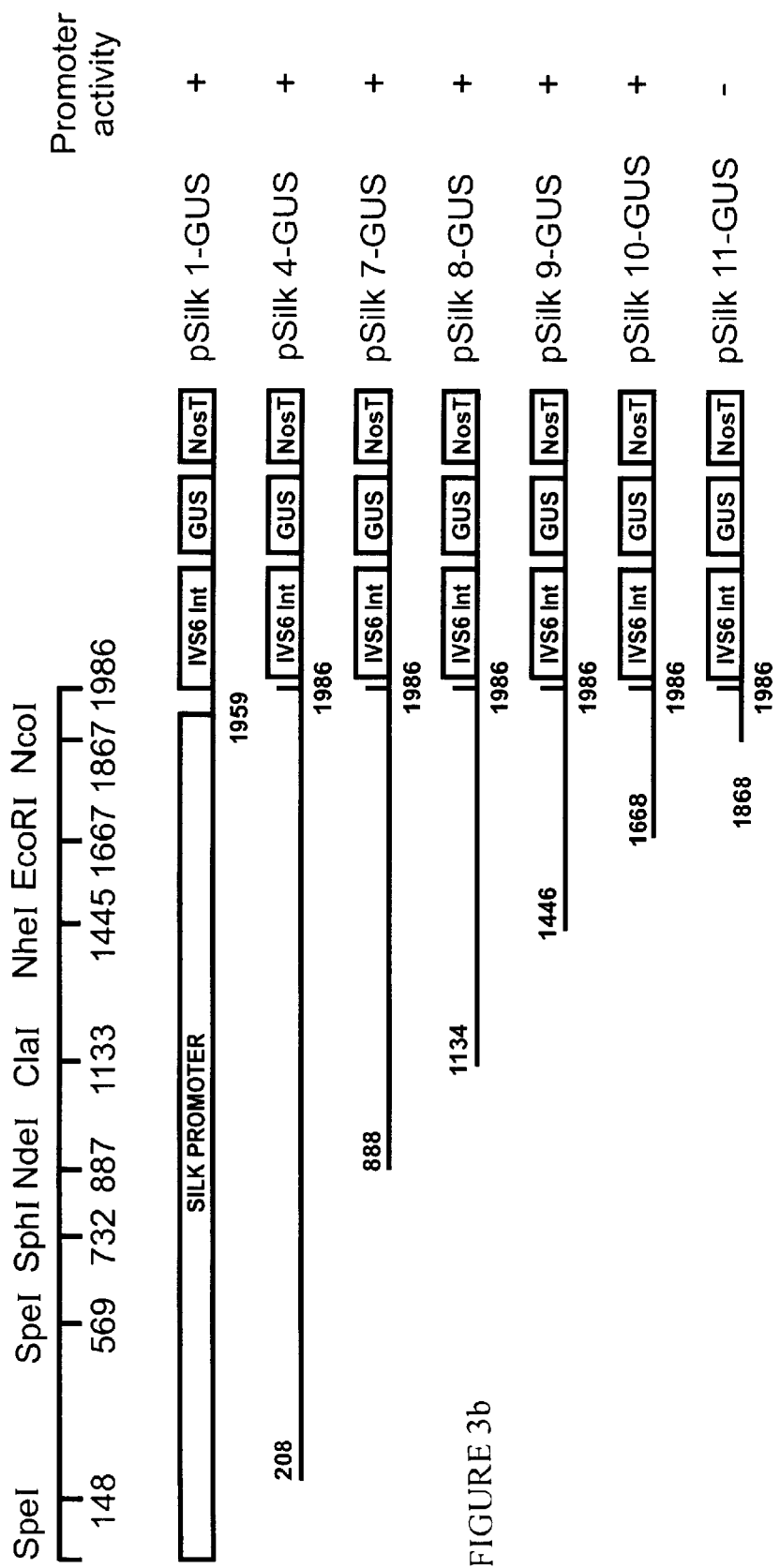

SEQUENCE LISTING

<160> NUMBER OF SEQ ID NOS: 4

<210> SEQ ID NO 1
<211> LENGTH: 3077
<212> TYPE: DNA
<213> ORGANISM: Zea mays
<220> FEATURE:
<221> NAME/KEY: promoter
<222> LOCATION: (1)..(1986)
<221> NAME/KEY: TATA_signal
<222> LOCATION: (1912)..(1917)
<221> NAME/KEY: misc_feature
<222> LOCATION: (1994)
<223> OTHER INFORMATION: transcription start site

<400> SEQUENCE: 1

| | | | | | |
|---|---|---|---|---|---|
| gatccttggg | atgatgggtt | cgagttgatg | aactcgatag | ccttgttaag | ttacccggta | 60 |
| cacgtgcaga | gccatctgag | gacgttaatg | acaaggattg | gtacatgtga | gcctaataac | 120 |
| ttgggagggc | tgtcacaaac | acagaggact | agtgtttcca | agaagctgca | acttttttca | 180 |
| tcttctctct | agttattgaa | gtgaaacatg | cttacgacgg | aatgtaaaca | tgggctaatc | 240 |
| cacatagggc | tttccgagtg | tacgtgaacg | aggggggaaaa | acagttccag | tgattaaaaa | 300 |
| ctaaattcta | ccacttgtgc | acaccctaat | ttttaattag | agaaattttt | taatacatgt | 360 |
| gtatattgaa | atattaatag | agtgtttggt | ttgaggaatc | aaatcatcca | aattgaagtg | 420 |
| gtgcatcatg | ggttcattcc | ccaaatttgg | tgtaatgact | ccattcctca | tattagtact | 480 |
| aactaactat | aaagaatgat | gtggtgatgg | attaactcat | tatattacac | aaaccaaaca | 540 |
| aaaatagtga | ggagtgagaa | gataagagac | tagttcattc | ctcgaaccaa | acacgccata | 600 |
| agtgttcact | cggattctcc | ggcctctagc | ttcgcccctc | aatgtaaaag | gagagagtcc | 660 |
| aagcacttat | cgcgtcgtgc | attgatatgc | gtgtccatcc | ccacgcttgt | acgacgcgct | 720 |
| tatgtccgca | tgctcaggct | cgctgtgagt | tattattgcg | cgactattag | cacgcatggt | 780 |
| ggccaccacg | ttcggagcca | gggttcacaa | aataggttaa | aatttaccaa | atccaaattc | 840 |
| aaaccattta | ttgaattttc | tcggtttgac | atccatttat | ccatacatat | gaccgattaa | 900 |
| tcggttctag | aaccgataag | ctgacaacac | atcaggtaaa | accaaatctc | ttgttttttgg | 960 |
| caaataaaaa | catgtttagg | tctcaacaat | tgaacaaaaa | atgtaccaaa | tgttatcaca | 1020 |
| agtttaatta | gaacatttag | tcatagtaat | ttaaaaagat | ttcaagtgaa | aagagagaaa | 1080 |
| aaatacccta | atcttagctc | ctattcaacc | gccaactaat | cagttctaca | catcgattta | 1140 |
| ttggtctaca | cttcgattat | ttttaatttg | aaatctatta | catattttga | aatttggttt | 1200 |
| cagcaaaaag | tcttcaaata | gttatcacaa | gtccaataac | atatttaatt | agtggtttaa | 1260 |
| atgcatcaca | tgatatggtt | tcatgattca | aatatattac | atgtaagcta | aggagctata | 1320 |
| agagagagcc | agaactgttt | ttagaggagc | cggagcactg | tcaaaggggc | ctttgtatgc | 1380 |
| ttcatcctag | agaggaatcg | aataaaagtc | gtgtgctact | tgttttcgcc | gttcattcct | 1440 |
| tgtggctagc | ttgtggcatt | acatccatag | tggtggtaaa | ttaacatgct | acatctttta | 1500 |
| ttgtgtcatc | ctgtggtcac | cagtggtttg | agataagtgg | aacttattgt | gccagcctag | 1560 |
| ttaaaggagc | tgttattcga | ctgcactagc | aatatgtact | actgtaggag | tactatattt | 1620 |
| cacatacgta | ggcagtctaa | ttctagttct | tattctaaac | gtcattgaat | tcactgctga | 1680 |
| ggaagcgatg | ggcaacaatg | aattgtcatg | cccgctctca | acaacacatg | tatgtagctc | 1740 |
| ctctggtact | agattgtaaa | tacacggccg | gctccatttt | ttttggatag | tagtactcca | 1800 |

| gtaataacag ttatgctggg tgcctgggtt gccaaccact catcagtgca cttattttg | 1860 |
| gtatagccat ggaagcttgt acagcttgca gccatgcttt cccggcttct ctataaaatt | 1920 |
| caggcactca tttccatatt ctcaccccaa ggccgggtcc tacgtagtcg aggactaccg | 1980 |
| caagaaatgg gggtcaacaa gtctgcagtt ctgcttggtg tggttttggt ctcagtcctt | 2040 |
| ctcggcttcc tggacgttgt gtacgcaagg gagctcactg aagccaatgg ctctggactg | 2100 |
| aagaataatg tgaagcctgc aggagagcct gggctcaagg atgagaagtg gtttggtggt | 2160 |
| agatacaagc atggtggagg gtatggaaac aaccagcccg gatacggcgg cggaggaaac | 2220 |
| agccaacctg gatacggcgg cggaggaaac agccagcccg gatacggtgg aggatacaag | 2280 |
| cgccatcacc ctggtggcgg ctacgggtct ggacaaggag ggcctggatg tggatgtgga | 2340 |
| ggagggtatg gaggtggcaa tggtagtcct gggtacggcg atgacaatgg tggtggcagt | 2400 |
| ggcactggcg gtggaaatgg caatgctggt gggtacggag gaggaggagg cggcggttat | 2460 |
| ggaggcggct acggcagtgg tagtggtaca gcaccaggag gcggatatca tggcggcggt | 2520 |
| ggtgcacaac gctacgctgg gcagaactag caagaacaac cccttatgct agtttatgtt | 2580 |
| aaataaacga tccattgttc atgtgactga gcaatttaag cagtgaagga tcttgactcg | 2640 |
| tgttatttgt gttaccatat gtattggttg ttttatgttt aagatgaatg tacaccgcta | 2700 |
| tttgtatgtc gaactcgttg catggagatg aaaaaaaaag gcacaaaaac atcagcaaac | 2760 |
| catgctttcc ttccggtcga ccagatttgg gctgatattt attgagtaaa aaaaaatct | 2820 |
| atctctggga gattgtttca gtaaaagct agagcgtgac attttgtagc ggaaaatcgg | 2880 |
| aacgaaaaca tgtccaacgt cgaaattatt gtatatattc taatggatat ataacgta | 2940 |
| atcagaagga aaattgtttc caagtcattt tttcacaatg caacagtcaa acatggatgc | 3000 |
| ggcgagcgaa ggatgcaggt gggttcccct gccgctccaa atcctgtaga gccctcctaa | 3060 |
| agactcccct aaaatta | 3077 |

<210> SEQ ID NO 2
<211> LENGTH: 1986
<212> TYPE: DNA
<213> ORGANISM: Zea mays
<220> FEATURE:
<221> NAME/KEY: promoter
<222> LOCATION: (1)..(1986)

<400> SEQUENCE: 2

| gatccttggg atgatgggtt cgagttgatg aactcgatag ccttgttaag ttacccggta | 60 |
| cacgtgcaga gccatctgag gacgttaatg acaaggattg gtacatgtga gcctaataac | 120 |
| ttgggagggc tgtcacaaac acagaggact agtgtttcca agaagctgca actttttca | 180 |
| tcttctctct agttattgaa gtgaaacatg cttacgacgg aatgtaaaca tgggctaatc | 240 |
| cacatagggc tttccgagtg tacgtgaacg aggggggaaaa acagttccag tgattaaaaa | 300 |
| ctaaattcta ccacttgtgc acaccctaat ttttaattag agaaattttt taatacatgt | 360 |
| gtatattgaa atattaatag agtgtttggt ttgaggaatc aaatcatcca aattgaagtg | 420 |
| gtgcatcatg ggttcattcc ccaaatttgg tgtaatgact ccattcctca tattagtact | 480 |
| aactaactat aaagaatgat gtggtgatgg attaactcat tatattacac aaaccaaaca | 540 |
| aaaatagtga gggagtgagaa gataagagac tagttcattc ctcgaaccaa acacgccata | 600 |
| agtgttcact cggattctcc ggcctctagc ttcgcccctc aatgtaaaag gagagagtcc | 660 |
| aagcacttat cgcgtcgtgc attgatatgc gtgtccatcc ccacgcttgt acgacgcgct | 720 |

-continued

```
tatgtccgca tgctcaggct cgctgtgagt tattattgcg cgactattag cacgcatggt    780
ggccaccacg ttcggagcca gggttcacaa aataggttaa aatttaccaa atccaaattc    840
aaaccattta ttgaattttc tcggtttgac atccatttat ccatacatat gaccgattaa    900
tcggttctag aaccgataag ctgacaaacac atcaggtaaa accaaatctc ttgtttttgg    960
caaataaaaa catgtttagg tctcaacaat tgaacaaaaa atgtaccaaa tgttatcaca   1020
agtttaatta gaacatttag tcatagtaat ttaaaaagat ttcaagtgaa aagagagaaa   1080
aaatacccta atcttagctc ctattcaacc gccaactaat cagttctaca catcgattta   1140
ttggtctaca cttcgattat ttttaatttg aaatctatta catattttga aatttggttt   1200
cagcaaaaag tcttcaaata gttatcacaa gtccaataac atatttaatt agtggtttaa   1260
atgcatcaca tgatatggtt tcatgattca aatatattac atgtaagcta aggagctata   1320
agagagagcc agaactgttt ttagaggagc cggagcactg tcaaggggc ctttgtatgc    1380 ttcatcctag agaggaatcg aataaaagtc gtgtgctact tgttttcgcc gttcattcct   1440
tgtggctagc ttgtggcatt acatccatag tggtggtaaa ttaacatgct acatctttta   1500
ttgtgtcatc ctgtggtcac cagtggtttg agataagtgg aacttattgt gccagcctag   1560
ttaaaggagc tgttattcga ctgcactagc aatatgtact actgtaggag tactatattt   1620
cacatacgta ggcagtctaa ttctagttct tattctaaac gtcattgaat tcactgctga   1680
ggaagcgatg ggcaacaatg aattgtcatg cccgctctca acaacacatg tatgtagctc   1740
ctctggtact agattgtaaa tacacggccg gctccatttt ttttggatag tagtactcca   1800
gtaataacag ttatgctggg tgcctgggtt gccaaccact catcagtgca cttattttg    1860 gtatagccat ggaagcttgt acagcttgca gccatgcttt cccggcttct ctataaaatt   1920
caggcactca tttccatatt ctcaccccaa ggccgggtcc tacgtagtcg aggactaccg   1980
caagaa                                                              1986
```

<210> SEQ ID NO 3
<211> LENGTH: 564
<212> TYPE: DNA
<213> ORGANISM: Zea mays
<220> FEATURE:
<221> NAME/KEY: exon
<222> LOCATION: (1)..(564)

<400> SEQUENCE: 3

```
atg ggg gtc aac aag tct gca gtt ctg ctt ggt gtg gtt ttg gtc tca     48 gtc ctt ctc ggc ttc ctg gac gtt gtg tac gca agg gag ctc act gaa     96 gcc aat ggc tct gga ctg aag aat aat gtg aag cct gca gga gag cct    144 ggg ctc aag gat gag aag tgg ttt ggt ggt aga tac aag cat ggt gga    192 ggg tat gga aac aac cag ccc gga tac ggc ggc gga gga aac agc caa    240 cct gga tac ggc ggc gga gga aac agc cag ccc gga tac ggt gga gga    288 tac aag cgc cat cac cct ggt ggc ggc tac ggg tct gga caa gga ggg    336 cct gga tgt gga tgt gga gga ggg tat gga ggt ggc aat ggt agt cct    384 ggg tac ggc gat gac aat ggt ggt ggc agt ggc act ggc ggt gga aat    432 ggc aat gct ggt ggg tac gga gga gga gga ggc ggc ggt tat gga ggc    480 ggc tac ggc agt ggt agt ggt aca gca cca gga ggc gga tat cat ggc    528 ggc ggt ggt gca caa cgc tac gct ggg cag aac tag                    564
```

```
<210> SEQ ID NO 4
<211> LENGTH: 187
<212> TYPE: PRT
<213> ORGANISM: Zea mays

<400> SEQUENCE: 4

Met Gly Val Asn Lys Ser Ala Val Leu Leu Gly Val Val Leu Val Ser
 1               5                  10                  15

Val Leu Leu Gly Phe Leu Asp Val Val Tyr Ala Arg Glu Leu Thr Glu
            20                  25                  30

Ala Asn Gly Ser Gly Leu Lys Asn Asn Val Lys Pro Ala Gly Glu Pro
        35                  40                  45

Gly Leu Lys Asp Glu Lys Trp Phe Gly Gly Arg Tyr Lys His Gly Gly
    50                  55                  60

Gly Tyr Gly Asn Asn Gln Pro Gly Tyr Gly Gly Gly Asn Ser Gln
65                  70                  75                  80

Pro Gly Tyr Gly Gly Gly Asn Ser Gln Pro Gly Tyr Gly Gly Gly
                85                  90                  95

Tyr Lys Arg His His Pro Gly Gly Tyr Gly Ser Gly Gln Gly Gly
            100                 105                 110

Pro Gly Cys Gly Cys Gly Gly Gly Tyr Gly Gly Gly Asn Gly Ser Pro
        115                 120                 125

Gly Tyr Gly Asp Asp Asn Gly Gly Gly Ser Gly Thr Gly Gly Gly Asn
    130                 135                 140

Gly Asn Ala Gly Gly Tyr Gly Gly Gly Gly Gly Gly Tyr Gly Gly
145                 150                 155                 160

Gly Tyr Gly Ser Gly Ser Gly Thr Ala Pro Gly Gly Gly Tyr His Gly
                165                 170                 175

Gly Gly Gly Ala Gln Arg Tyr Ala Gly Gln Asn
            180                 185
```

CORN SILK GENE AND REGULATORY REGION

This application is a continuation-in-part of U.S. application Ser. No. 09/412,704, filed Oct. 5, 1999, now abandoned.

The present invention relates to genes isolated from stigma tissues. More specifically, the present invention relates to a gene and regulatory region isolated from corn silk.

BACKGROUND OF THE INVENTION

The silk is part of the female reproductive organ in corn. It is a long hairy structure attached to the ovary. Pollen grains lodge upon the silk, they germinate and the pollen tubes grow down the hair into the silk to reach the ovules (Bonnett, O. T., 1948). The corn silk corresponds to the stigma in typical flowers (Heslop-Harrison et al, 1984). The stigma is responsible for capturing and selecting compatible pollen grains and for facilitating their germination.

The silk strands are mainly constituted of one external epidermal layer surrounding many cell layers of parenchyma tissues, and of vascular bundles located within the parenchyma tissue. The vascular bundle areas include pollen transmitting tissues, xylem elements, sieve tube elements and companion cells. The companion cells are morphologically and physiologically associated with the sieve tubes elements. Companion cells are key players in the phloem loading of assimilates and the synthesis of proteins targeted to enucleate sieve tubes and their functions require transport through plasmodesmata to sieve elements.

Genes and promoters that have been shown to function primarily in the stigma have been identified primarily in a few dicot species. They include proteinase inhibitors from *Nicotiana alara* (Atkinson et al, 1993), chitinases from *Petunia hybrida* (Leung, 1992) and genes involved in the sporophytic self-incompatibility system of Brassica (Dzelzkalns et al, 1993; Goring et al, 1993; Nasrallah and Nasrallah, 1993; Robert et al, 1994; Trick and Heizmann, 1992). A gene from soybean, ENOD40(2) has been found to function in root and stigma (Mirabella et al, 1999).

A number of genes have been shown to be preferentially expressed in the stigma of Brassica that correspond to genes associated with SI: SLG (S-locus glycoprotein), SRK (S receptor kinase; U.S. Pat. No. 5,484,905) or SLR (S-locus-related; WO94/25613) genes (for review: Nasrallah, J. B., Nasrallah, M. E. *Plant Cell* 5:1325–1335 (1993)). $SRK_6$ is reported to be preferentially expressed in pistil and anther tissues (U.S. Pat. No. 5,484,905). U.S. Pat. No. 5,585,543 discloses the use of the S-gene for altering self incompatibility. The $S_3$ promoter was found to confer expression within the pistil.

Another example of a gene expressed in the Brassica stigma is Pis 63 (U.S. Pat. No. 5,907,093; Robert, L. S. et al Plant Mol. Biol 26: 1217–1222 (1994)). The preparation of plants with female sterility based on a style-stigma specific "STMG" gene and derived constructs using PSTMG promoter cassettes is disclosed in U.S. Pat. No. 5,633,441. These constructs include transcriptional fusions comprising barnase, papain or RNAse. Related U.S. Pat. No. 5,767,374 also discloses female sterile plants which are transformed with foreign DNA encoding a female sterility protein and a promoter which may be tissue specific, for example, a stigma-specific promoter. However, in both U.S. Pat. Nos. 5,633,441 and 5,767,374 no silk-specific promoters or their use, is disclosed. U.S. Pat. No. 5,723,763 discloses a method for identifying a tissue-specific promoter including stigma specific promoters.

An example of a promoter expressed in the companion cells of *Arabidopsis thaliana* leaves, stems and sepals is AtSUC2 (Truernit, E. and Sauer, N. Planta 196:564–570 (1995)). This promoter has low or undetectable activity in many other tissues of the transgenic plants, including petals, anthers and pistils.

The promoters identified above have been isolated from dicot plants. None of these promoters have been isolated from corn silk, nor is it known if these promoters may function in corn silk. U.S. Pat. Nos. 5,608,143 and 5,364,780 disclose nucleic acid promoter fragments from corn, however, no promoters are reported from silk. U.S. Pat. No. 5,589,610 discloses stamen specific promoters from corn. No stigma-specific promoters are disclosed.

The silk is also one of the two principal routes of invasion by the fungus *Fusarium graminearum* in corn. Fungal spores lodge upon the silk, germinate and the mycelia grow down the strands, either inside or outside, until they reach the ovules where the infection develops further. Expression of certain defence genes in silk may increase the resistance of corn to Fusarium species, however, no silk-specific promoters have been identified that could be used for this purpose. Furthermore, it is not known if stigma specific promoters isolated from dicot species such as *Brassica napus* would be functional in corn.

U.S. Pat. No. 5,859,351 discloses the Prf gene (from tomato) which encodes a protein that confers phytopathogenic resistance to transgenic plants against such pathogens as Pseudomonas and Xanthomonas. The use of silk- or monocot-specific promoters is not noted. U.S. Pat. No. 5,670,349 discloses a HMG2 promoter responsive to pathogen infection, pest infection and chemical induction that can be used to drive expression of disease and pest resistance genes of interest. The promoter is active in pollen and mature fruit tissues, however, there is no disclosure of whether it is active in corn silk.

WO 98/18939 discloses a nucleotide sequence encoding a salicylic acid-induced protein (SIP) kinase which may activate plant defences against microbial pathogens, and may be activated by, for example, a microbial pathogen, or an elicitor such as salicylic acid. Transformation of plants with this kinase enhances disease resistance to certain pathogens by inducing certain defence responses in a plant. The use of CaMV 35S is discussed, but tissue specific silk, or pistil/stigma, promoters are not discussed.

WO 99/02655 discloses nucleic acids encoding protein kinase genes, that can be induced by pathogen invasion or elicitor treatment. Plants transformed with such nucleic acids have enhanced pathogen resistance. Inducible regulatory elements flanking the nucleic acid may also be included in the transformed plant, however, no mention is made of silk or stigma specific promoters.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to genes isolated from stigma tissues. More specifically, the present invention relates to a gene and regulatory region isolated from corn silk.

According to the present invention there is provided a regulatory region comprising an isolated nucleic acid obtained from corn silk.

This invention is also directed to an isolated nucleic acid comprising a silk-specific regulatory region or a fragment thereof, or a nucleic acid that is substantially homologous with the silk-specific regulatory region or a fragment thereof, wherein the nucleic acid that is substantially homologous with the silk regulatory region or fragment thereof, exhibits silk activity.

The present invention also provides for an isolated nucleic acid comprising nucleotides 1 to about 1986 of SEQ ID NO:2 or a fragment thereof, or a nucleic acid that is substantially homologous with nucleotides 1 to about 1986 of SEQ ID NO:2 or a fragment thereof, wherein the nucleic acid that is substantially homologous with nucleotides 1 to about 1986 of SEQ ID NO:2 or a fragment thereof, exhibits silk activity.

The present invention also pertains to an isolated nucleic acid comprising nucleotides 1 to about 1959, from about 208 to about 1986, from about 888 to about 1986, from about 1134 to about 1986, from about 1446 to about 1986, from about 1668 to about 1986, or from about 1868 to about 1986 of SEQ ID NO:2.

Furthermore, the present invention is directed to an isolated nucleic acid comprising nucleotides from about 1668 to about 1868 of SEQ ID NO:2.

This invention includes a chimeric construct comprising the regulatory region comprising an isolated nucleic acid obtained from corn silk in operative association with a gene of interest. It also is directed to a vector comprising the chimeric construct, and a transgenic plant comprising the vector.

The present invention is directed to a chimeric construct comprising an isolated nucleic acid obtained from corn silk in operative association with a heterologous regulatory element, to a vector comprising this chimeric construct, to a transgenic plant cell comprising this vector, to transgenic seed comprising this vector, and to a transgenic plant comprising this vector.

The present invention provides for a method of producing a female sterile plant comprising:

i) transforming a plant for which female sterility is desired with a regulatory region comprising an isolated nucleic acid obtained from corn silk, inoperative association with a gene that encodes a protein involved in inhibiting pistil development, pollen stigma interactions, pollen tube growth or fertilization, or a combination thereof to produce a transformed plant; and ii) growing said transformed plant.

Also included within this invention is a method of producing a plant with increased pathogen resistance comprising:

i) transforming a plant with a regulatory region comprising an isolated nucleic acid obtained from corn silk, inoperative association with a gene that encodes a protein involved in inducing pathogen resistance, to produce a transformed plant; and ii) growing said transformed plant.

The present invention is also directed to a method of producing a plant expressing a gene of interest within the pistil comprising:

i) transforming a plant with a vector, the vector comprising a regulatory region obtained from corn silk in operative association with a gene of interest, to produce a transforrned plant; and ii) growing said transformed plant.

The regulatory region obtained from corn silk may be used to direct the expression of a gene of interest in the stigma from a range of plants. Furthermore, the activity of the regulatory region of the present invention may be modified by the presence of other regulatory regions, for example, enhancers, core promoter elements and the like, in operative association with a regulatory region of the present invention.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIGS. 3a, 3b and 3c show a restriction map and set of deletion constructs of the C3 regulatory region as well as transient expression in bombarded corn silk. FIG. 3(a) is a diagrammatic representation of the regulatory region of C3 (SEQ ID NO:2). FIG. 3(b) shows the construct containing the full length promoter, pSilk4-GUS and a series of deletion constructs including pSilk1-GUS, pSilk7-GUS to pSilk11-GUS. Every construct is fused to GUS. Promoter activity, as observed by the presence (+) or absence (−) of GUS activity in transient assay of bombarded corn silk, is indicated in the right column. FIG. 3(c) is a diagrammatic representation of pSilk4-int-RPLC4-Nos.

FIG. 7(a) shows strands of corn silk as viewed using a dissecting microscope. FIG. 7(b) shows a cryosection of part of a stained silk strand showing GUS expression localised to the vascular elements, and in the companion cells of the vascular bundles.

FIG. 8(a) shows an example where expression was specific to the stigma. FIG. 8(b) shows an example where expression was observed in the stigma as well as in other parts of the flower.

DESCRIPTION OF PREFERRED EMBODIMENT

Figure 1:
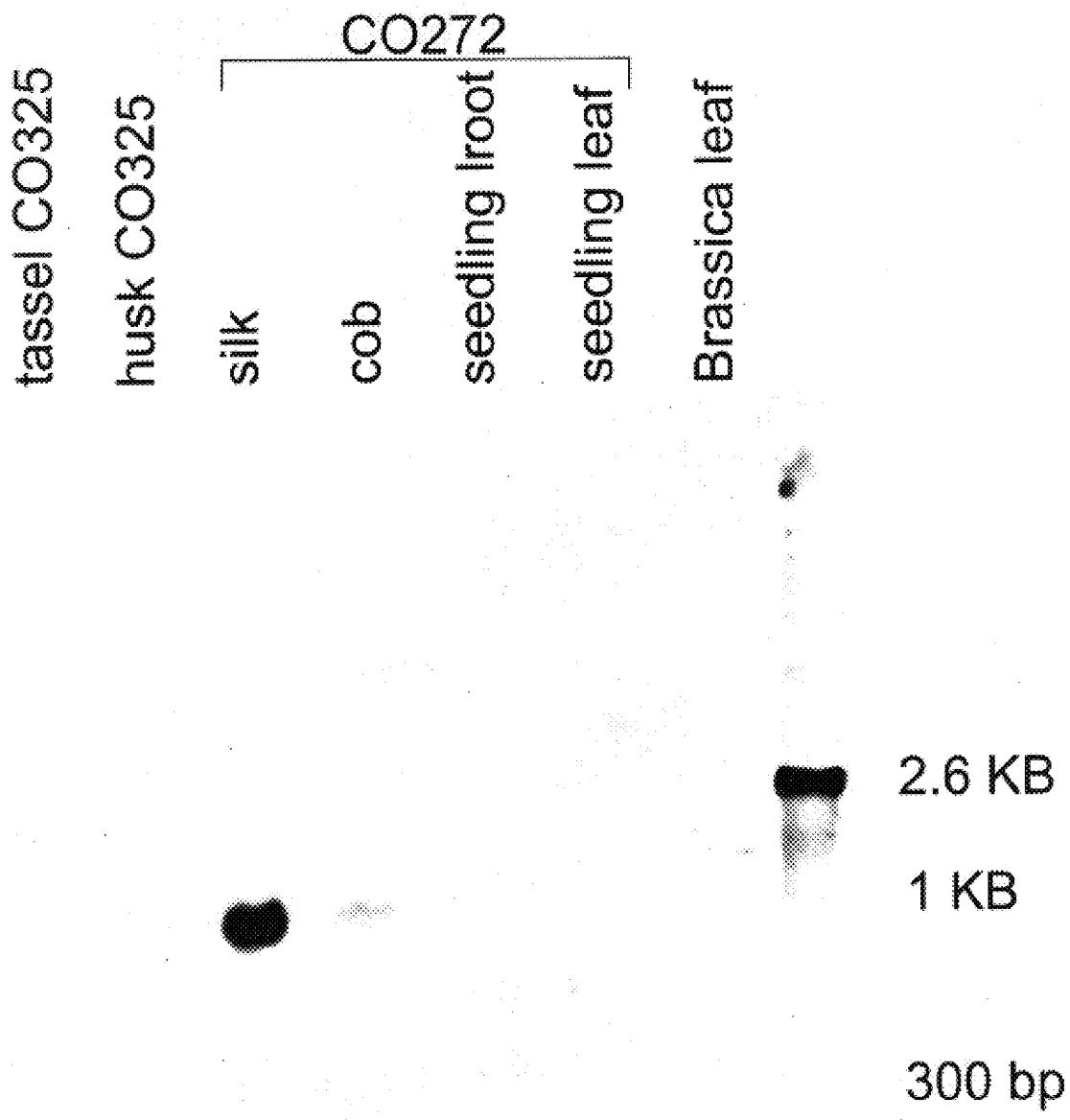
FIG. 1 shows the expression of C3 genes in different corn tissues. Northern blot analysis of different corn tissues was carried out using C3 cDNA labelled with DIG as a probe. Each lane was loaded with 20 μg total RNA, and the blot exposed for 3 minutes. Lanes from left to right, tassel, husk, silk, cob, root leaf and RNA molecular weight marker. The low level of expression associated with the cob may be due to silk strands attached to each kernel which are difficult to remove at this stage of development.

The present invention relates to genes isolated from stigma tissues. More specifically, the present invention relates to a gene and regulatory region isolated from corn silk.

The following description is of a preferred embodiment by way of example only and without limitation to the combination of features necessary for carrying the invention into effect.

The present invention relates to genes, and analogs or nucleotide sequences substantially homologous thereto, isolated from a corn silk library. Examples of such nucleotide sequences include, but are not limited to, C3 (SEQ ID NO:1), C1 and A1 (closely related to C3). These sequences are expressed preferentially in corn silk. The C3 gene comprises a regulatory region (nucleotides 1–1986 of SEQ ID NO:1; SEQ ID NO 2), a coding region (nucleotides 1987–2570 of SEQ ID NO:1; SEQ ID NO:3) and a 3'region (nucleotides 2571–3077 of SEQ ID NO:1). The regulatory region of C3, or fragments thereof may be used to direct expression of a gene of interest within stigma cells of both monocot and dicot plants.

A search of the GenBank database (FASTAp) indicates that the 5' and 3'regions of C3 exhibits no significant homology to known sequences, aside from a partial Ds-like sequence located within the 5' region 1200 bp upstream of the beginning of the coding region, and portions of a cystathione synthase. The open reading frame of C3 (see SEQ ID NO:3 for the DNA sequence and SEQ ID NO:4 for the amino acid sequence) comprises a glycine-rich domain and exhibits some resemblance to similar domains in other glycine-rich proteins. Analysis of the open reading frame of C3 (SEQ ID NO:4), using protein prediction programs, shows the presence of a transit peptide in the 5' region, as well as a heme binding domain. The C3 protein is also rich in cysteine, indicating possible disulfide bridges. Without wishing to be bound by theory, these analysis indicates that the protein falls into the class of metal binding, disulfide bridge small peptides, with possible relations to wheat germ agglutinin isolectin2 based on predicted protein folding.

Many proteins with glycine-rich domains have been identified in plants with functions such as RNA-binding proteins (Hirose et al, 1993; Ludevid et al, 1992; Nicolas et al, 1997), cell wall composition/repair proteins (Condit, 1993; Lei et al, 1991; Ryser et al, 1997; Yasuda et al, 1997), proteins present in vascular tissues (Cheng et al, 1996; Parsons and Mattoo, 1994) or yet unidentified, tissue-specific functions (de Oliveira et al, 1993; Goddemeier et al, 1998; Quigley et al, 1991; Sakuta et al, 1998).

By "regulatory element" or "regulatory region", it is meant a portion of nucleic acid typically, but not always, upstream of a gene, and may be comprised of either DNA or RNA, or both DNA and RNA. The regulatory elements of the present invention includes those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. Enhancer elements may be repeated thereby further increasing the enhancing effect of an enhancer element on a regulatory region. "Regulatory elements" as used herein, also includes elements that are active following transcription or translation initiation, for example, regulatory elements that modulate gene expression such as translational and transcriptional enhancers, translational and transcriptional repressors, and mRNA stability or instability determinants.

In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, of the present invention may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the present invention may be operatively associated with constitutive, inducible, or tissue specific promoters or fragment thereof, to modulate the activity of such promoters within desired tissues within plant cells.

An "analogue" of the regulatory elements of the present invention includes any substitution, deletion, or addition to the sequence of a regulatory element provided that said analogue maintains at least one regulatory property associated with the activity of the regulatory element of the present invention. Such properties include directing organ specificity, tissue specificity, or a combination thereof, or temporal activity, or developmental activity, or a combination thereof.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well.

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods.

A constitutive regulatory element directs the expression of a gene throughout the various pans of a plant and continuously throughout plant development. Examples of known constitutive regulatory elements include promoters associated with the CaMV 35S transcript. (Odell et al., 1985, Nature, 313: 810–812), the rice actin 1 (Zhang et al, 1991. Plant Cell, 3: 1155–1165) and triosephosphate isomerase 1 (Xu et al, 1994, Plant Physiol. 106: 459–467) genes, the maize ubiquitin 1 gene (Cornejo et al, 1993, Plant Mol. Biol. 29: 637–646), the Arobidopsis ubiquitin 1 and 6 genes (Holtorf et al, 1995, Plant Mol. Biol. 29: 637–646), the tobacco translational initiation factor 4A gene (Mandel et al, 1995 Plant Mol. Biol. 29: 995–1004), and T1278 from tobacco (WO 97/28268). Regulatory elements derived from these constitutive regulatory elements, for example but not limited to core promoter elements, or enhancers, may be used in operative association with the regulatory element, or a fragment thereof, of the present invention.

By "silk activity" it is meant activity associated with a regulatory region as defined above, that is predominantly directed within silk tissue. Typically a regulatory region that exhibits silk activity would be obtained from silk tissue, however, analogs or fragments thereof, of genes associated with silk tissue, or regulatory regions or fragments thereof, obtained from genes associated with other tissues may also exhibit silk activity. Furthermore, fragments of the regulatory region of the present invention may also be combined with other endogenous or heterologous regulatory elements so that the chimeric regulatory region exhibits silk activity. It is to be understood that a regulatory region or a portion thereof, that exhibits silk activity, may also exhibit activity with pistil tissues, including for example the stigma, style or both the stigma and style, of other plants. An example, which is not to be considered limiting in any manner, of a regulatory element exhibiting silk activity comprises nucleotides 1–1986 of SEQ ID NO:1, or a fragment or analogue thereof.

The present invention is further directed to a chimeric gene construct containing a gene of interest operatively linked to a regulatory element of the present invention. Furthermore the present invention is directed to a chimeric gene construct comprising a regulatory element obtained from a silk regulatory region, for example but not restricted to, the C3 regulatory region in combination with another regulatory element and a gene of interest.

Any exogenous gene of interest can be used and manipulated according to the present invention to result in the expression of the exogenous gene of interest.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The chimeric construct may comprise the 3' untranslated region obtained from C3.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase, and green fluorescence protein are useful.

Also considered part of this invention are transgenic plants containing the chimeric gene construct comprising a regulatory element of the present invention. Therefore, the present invention is directed to a method of producing a plant expressing a gene of interest within the pistil comprising:

i) transforming a plant with a vector, the vector comprising a regulatory region, a fragment, or an analog thereof, exhibiting silk activity in operative association with a gene of interest, to produce a transformed plant; and ii) growing said transformed plant.

By "gene of interest" or "coding sequence of interest" it is meant any gene that is to be expressed within a host organism. Such a gene, or coding sequence of interest may include, but is not limited to, a gene that encodes a protein directed at improving plant defence against pathogens such as, in the case of corn, *Fusarium graminearum,* the causal agent of pink ear rot of corn and fusarium head blight of wheat. Other pathogen induced proteins that may be considered a gene of interest include, but are not limited to, calcium dependant protein kinase (CDPK), or a CDPK related peptide (WO 99/02655), MAP kinases, for example, p46 kinase (Usami et al 1995 PNAS 92:8660–8664; Seo et al 1995 Science 270:1988–1992), p47 kinase (Suzuki et al 1995 Plant Cell 7:639–647), salicyclic acid-induced protein kinase (SIP kinase; WO 98/18939), Prf gene (U.S. Pat. No. 5,859,351), Pto protein kinase from tomato (Martin et al 1993 Science 262:1432–1436; Zho et al 1995 Cell 83:925–935), or a modified form of the ribosomal protein RPL3 from rice (WO 99/09173, which is incorporated herein by reference).

Therefore, this invention is also directed to a method of producing a plant that exhibits improved response to a plant pathogen within silk tissue. This method comprises transforming a plant with a regulatory region exhibiting silk activity, or a fragment thereof, in operative association with a gene that encodes a protein of interest, for example, one that is involved in inducing or improving a pathogen response within the stigma, style or pistil, or a combination thereof to produce a transformed plant, optionally confirming the presence of said gene in said transformed plant, and growing said transformed plant.

Furthermore, genes of interest may also include genes encoding proteins that impart sterility to the plant, for example, but not limited to proteins that are cytotoxic to plant cells, including the pectate lyase gene pelE, from *Erwinia chrysanthermi* (Kenn et al 1986, J. Bacteroil 168:595), diphtheria toxin A-chain gene (Greenfield et al 1983 PNAS 80:6853; Palmiter et al 1987 Cell 50:435), T-urf13 gene from cms-T maize mitochondrial genomes (Braun et al 1990 Plant Cell 2:153; Dewey et al. 1987 PNAS 84:5374), CytA toxin gene from *Bacillus thuringiensis* Israeliensis that causes cell membrane disruption (McLean et al 1987 J. Bacteriol 169:1017; U.S. Pat. No. 4,918,006), Dnases, Rnases, (U.S. Pat. No. 5,633,441, which is incorporated by reference) proteases, or a gene of interest may express anti-sense RNA. A gene of interest may also encode a protein involved in inhibiting pistil development, pollen stigma interactions, pollen tube growth or fertilization, or a combination thereof.

By introducing a gene that encodes at least one protein that may be involved in imparting sterility into the pistil of a plant, for example, but not limited to the silk of corn, pollination, pollen tube development, or fertilization processes of the plant may be controlled. Examples of such methods may be found in U.S. Pat. Nos. 5,633,441, 5,907,083, 5,723,763, 5,767,374 and WO 94/25613 (which are incorporated by reference) which are directed to or disclose methods for imparting female sterility to plants. Analogous methods for imparting male sterility to plants are also well known in the art (e.g. U.S. Pat. No. 5,659,124, which is incorporated by reference).

Therefore, this invention is also directed to a method of producing a female sterile plant that comprises transforming a plant for which female sterility is desired with a silk regulatory region, or a fragment thereof, in operative association with a gene that encodes a protein involved in inhibiting pistil development, pollen-stigma interactions, pollen tube growth or fertilization, or a combination thereof to produce a transformed plant, optionally confirming the presence of said gene in said transformed plant, and growing said transformed plant.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology,* Academy Press, New York VIII, pp. 421–463 (1988, which is incorporated by reference); Geierson and Corey, *Plant Molecular Biology,* 2d Ed. (1988); and Miki and Iyer, *Fundamentals of Gene Transfer in Plants.* In *Plant Metabolism,* 2d Ed. D T. Dennis, D H Turpin, D D Lefebrve, D B Layzell (eds), Addison Wesly, Langmans Ltd. London, pp. 561–579 (1997, which is incorporated by reference). The present invention further includes a suitable vector comprising the chimeric gene construct.

The DNA sequences of the present invention thus include, but are not limited to, the DNA sequence of SEQ ID NO: 1, and fragments thereof. These fragments include the coding region of C3 as defined by nucleotides 1944–2759 of SEQ ID NO:1, the regulatory region of C3, as defined by nucleotides 1–1986 of SEQ ID NO:1 (SEQ ID NO:2) and fragments thereof, for example but not limited to, fragments outlined in FIG. 3(b), and the 3' region of the C3 gene as defined by nucleotides 2760–3077 of SEQ ID NO:1.

The present invention is also directed to analogues of, or nucleic acid sequences comprising about 80% similarity with the coding region of C3 defined by nucleotides 1944–2759 of SEQ ID NO:1, the regulatory region, as defined by nucleotides 1–1986 of SEQ ID NO:1 and fragments thereof, for example but not limited to, fragments outlined in FIG. 3(b), and the 3' region of the C3 gene as defined by nucleotides 2760–3077 of SEQ ID NO:1. Analogues (defined above), include those DNA sequences which exhibit substantial homology with the above sequences. By substantial homology it is meant sequences and hybridize under stringent hybridization conditions (see Maniatis et al., in Molecular Cloning (A Laboratory Manual), Cold Spring Harbor Laboratory, 1982, p. 387–389, which is incorporated by reference) to the DNA sequence of interest, for example but not limited to, SEQ ID NO: 2 or a fragment thereof, and the fragments outlined in FIG. 4(b), provided that the hybridizing sequences maintain silk activity as defined herein.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 4×SSC at 42° C. Analogues also include those DNA sequences which hybridize to any one of the sequences of SEQ ID NO's: 2 to 3 under relaxed hybridization conditions, provided that the sequences maintain at least one regulatory property of the activity of the regulatory element. Examples of such non-stringent conditions includes hybridization in 4×SSC at 50° C. or with 30–40% formamide at 42° C.

For the use of DIG-labelled DNA probes (15 ng/ml of probe in Easy Hyb buffer; Boehringer Mannheim), an example of stringent hybridization conditions may include hybridization at 50° C. followed by washes, including a final wash in 0.1×SSC, 0.1% SDS at 68° C.

Figure 2:
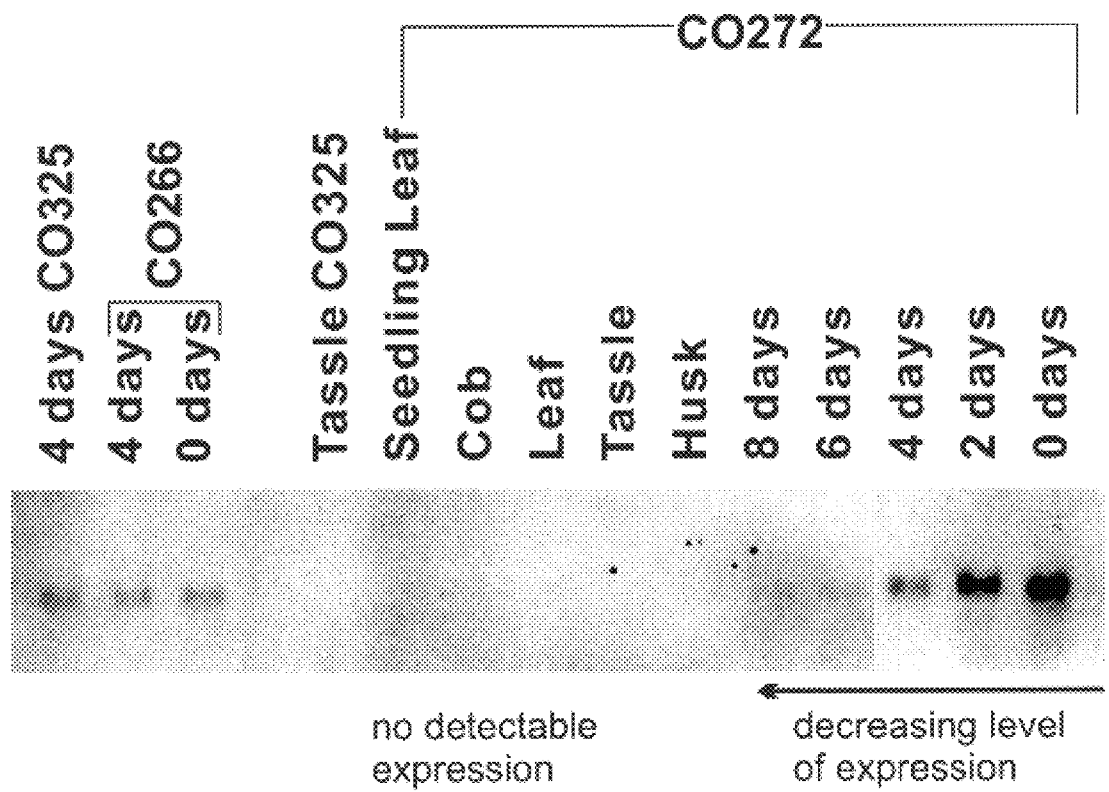
FIG. 2 shows tissue and developmental expression of the C3 gene. Northern blot analysis of C3 expression in a range of tissues including tassel, seedling, leaf, cob, and husk, as well as C3 expression in developing silk over an eight day period (days post silk emergence) in corn genotype CO272. Expression in developing silk from other corn genotypes is also shown (CO325, CO266). At day 0, the silk just emerges from the cob on the plant. Fertilization typically occurs within 2 days, and silk begins to deteriorate after fertilization, or after 5 to 8 days if unfertilized. Each lane was loaded with 15 μg total RNA and probed using C3 cDNA.

Northern analysis of a range of tissues including tassel, husk, silk, cob, root and young leaf, indicates that the RNA for C3 accumulates to a high level in silk tissues (FIGS. 1 and 2). Low levels of RNA that hybridized to C3 were observed in developing cob tissues (FIG. 1), however, this may be due to contamination of the cob tissue with silk fragments that remain attached to each kernel of the cob.

The regulatory region of C3 (SEQ ID NO:2; nucleotides 1–1986 of SEQ ID NO:1; also see FIG. 3(a)), and fragments thereof (pSilk1, pSilk4, and pSilk 7–11; see FIG. 3(b)), has been characterized. Regulatory region activity was observed for all deletion constructs except pSilk11-GUS demonstrating that nucleotides 1 to about 1668 of SEQ ID NO's:1 or 2, or a fragment thereof, may be used to drive expression of a gene of interest, and that nucleotides 1868–1986 of SEQ ID NO's:1 or 2 are not sufficient by themselves to carry activity in silk tissues. The results also demonstrate that the region between about 1668 to about 1868 of SEQ ID NO's:1 or 2 is required for regulatory region activity in corn silk. Therefore, the present invention is also directed to a chimeric gene construct comprising a regulatory region comprising nucleotides from about 1668 to about 1868 of SEQ ID NO's:1 or 2. Furthermore this invention pertains to chimeric gene constructs comprising a regulatory region comprising nucleotides 1 to about 1668 of SEQ ID NO's:1 or 2, or a fragment thereof.

Figure 3C:
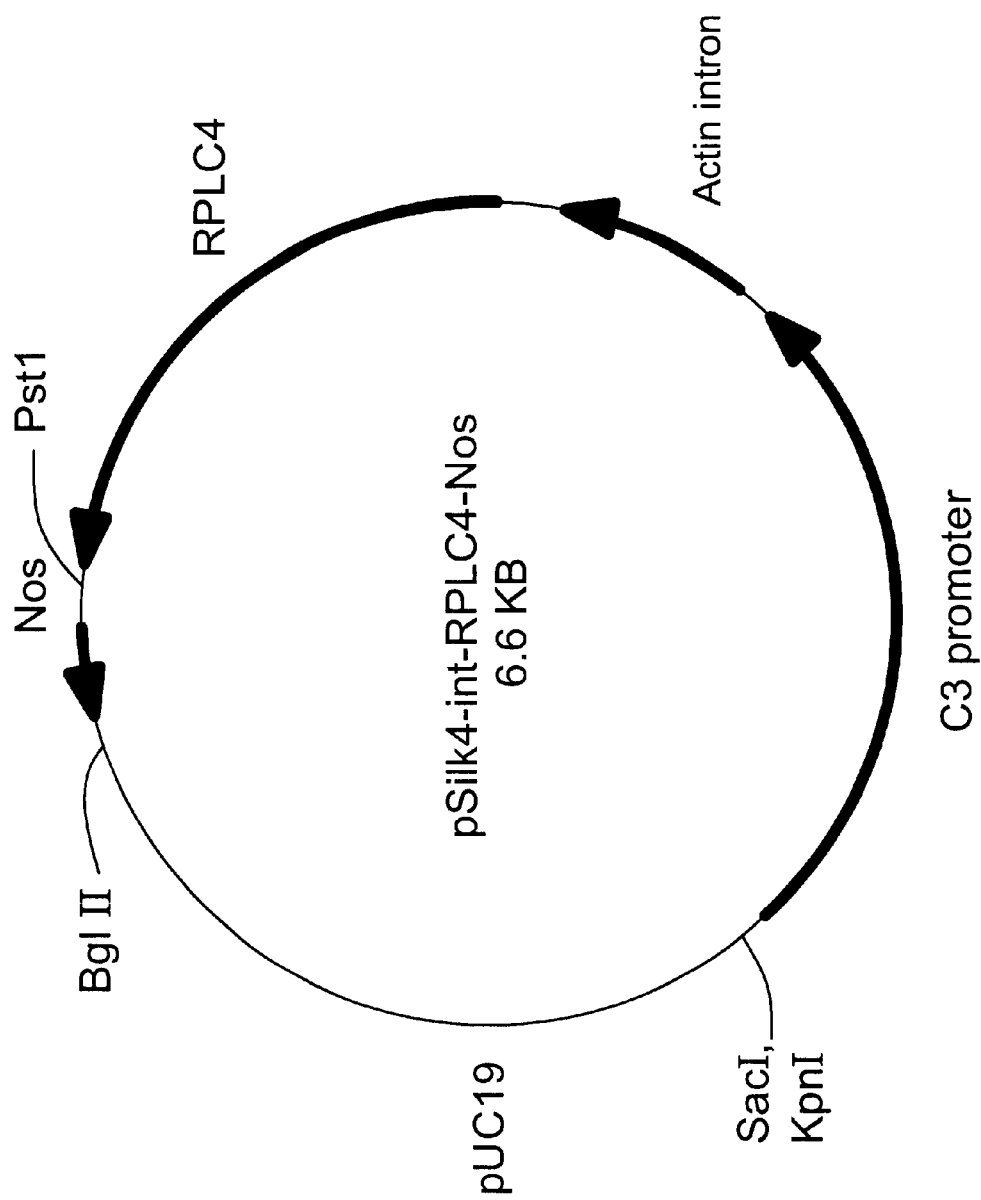
Figure 4:
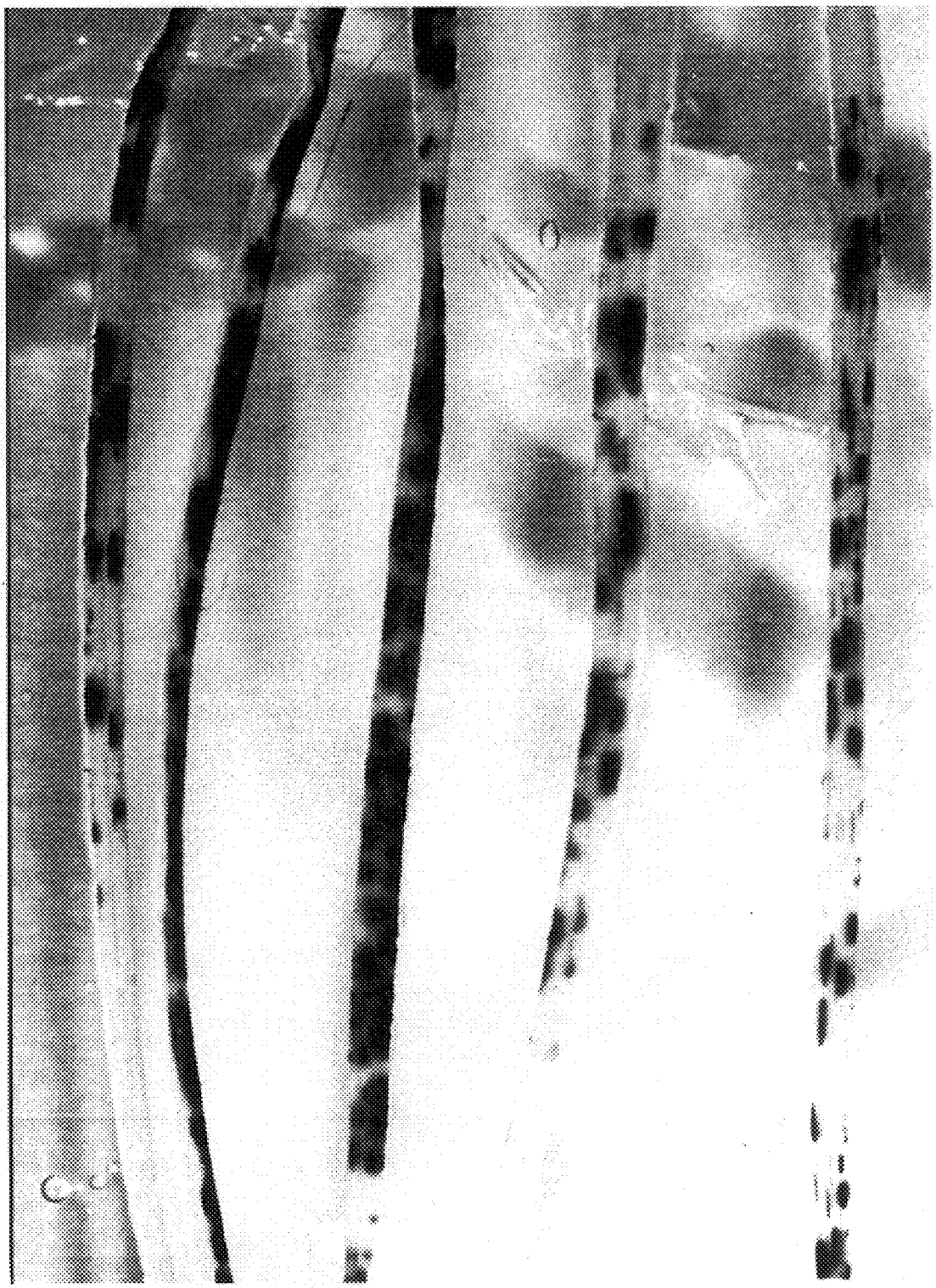
FIG. 4 shows GUS expression in isolated corn silk. The C3 regulatory region was fused with GUS (pSilk4) and introduced into corn silk using particle bombardment followed by detection of GUS activity in transient assay.
Figure 5:
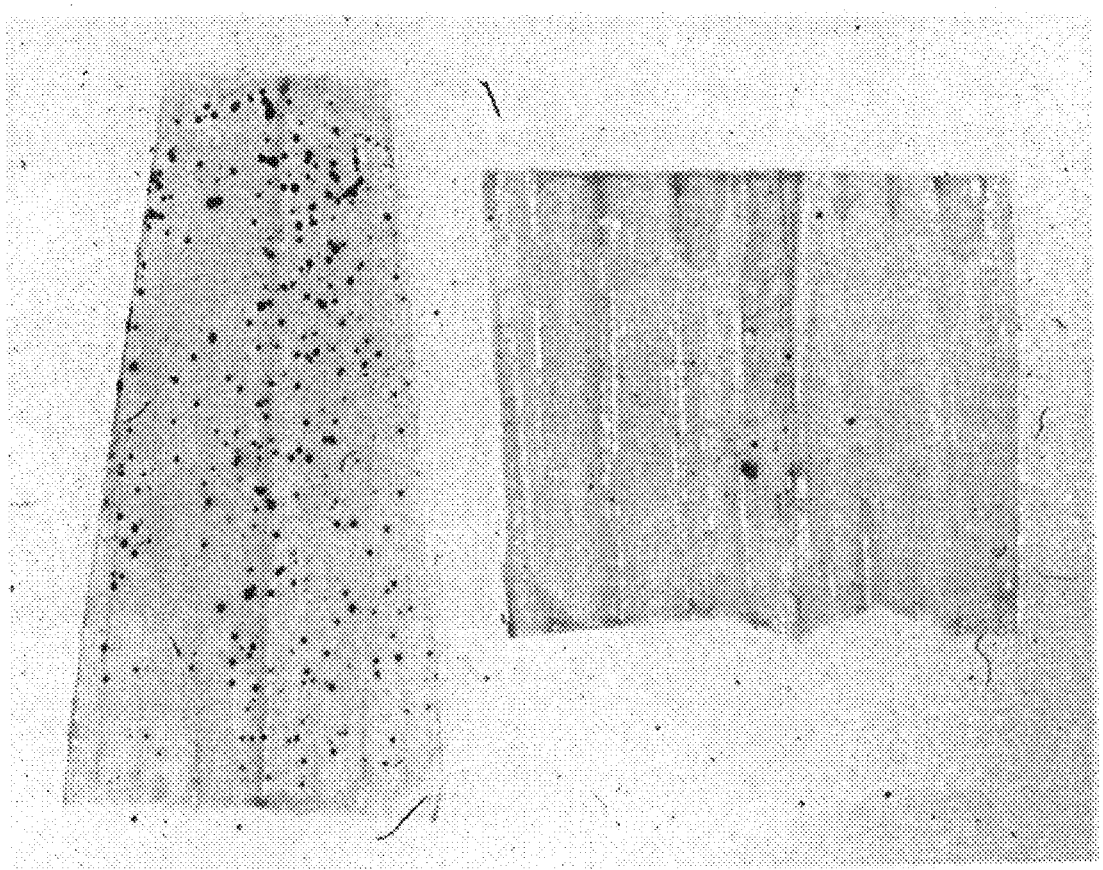
FIG. 5 shows GUS expression in corn leaf. The C3 regulatory region (psilk4), and the regulatory region obtained from Actin (pActin) were fused to GUS and introduced transiently into corn leaf using particle bombardment followed by detection of GUS activity. pActin is a constitutive promoter that is active in monocot tissues.

Transient expression analysis using a portion of the regulatory region, pSilk4 (nucleotides from about 208 to about 1986 of SEQ ID NO:1), fused to the marker gene B-glucuronidase (GUS) for bombardment directs preferential expression of GUS to high level in silk tissues (FIG. 4). Transient expression was also observed using pSilk1-GUS and pSilk7 to 10 GUS fusions (see FIG. 3(b)). No activity was detected with the construct pSILK11-GUS. Comparison of the level of GUS expression in corn leaf, directed by the regulatory region of C3 (pSilk4-GUS) with the level of GUS expression driven by the constitutive promoter obtained from Actin, indicates that in maize the regulatory region is not significantly active in leaf tissues (FIG. 5).

Figure 8A:
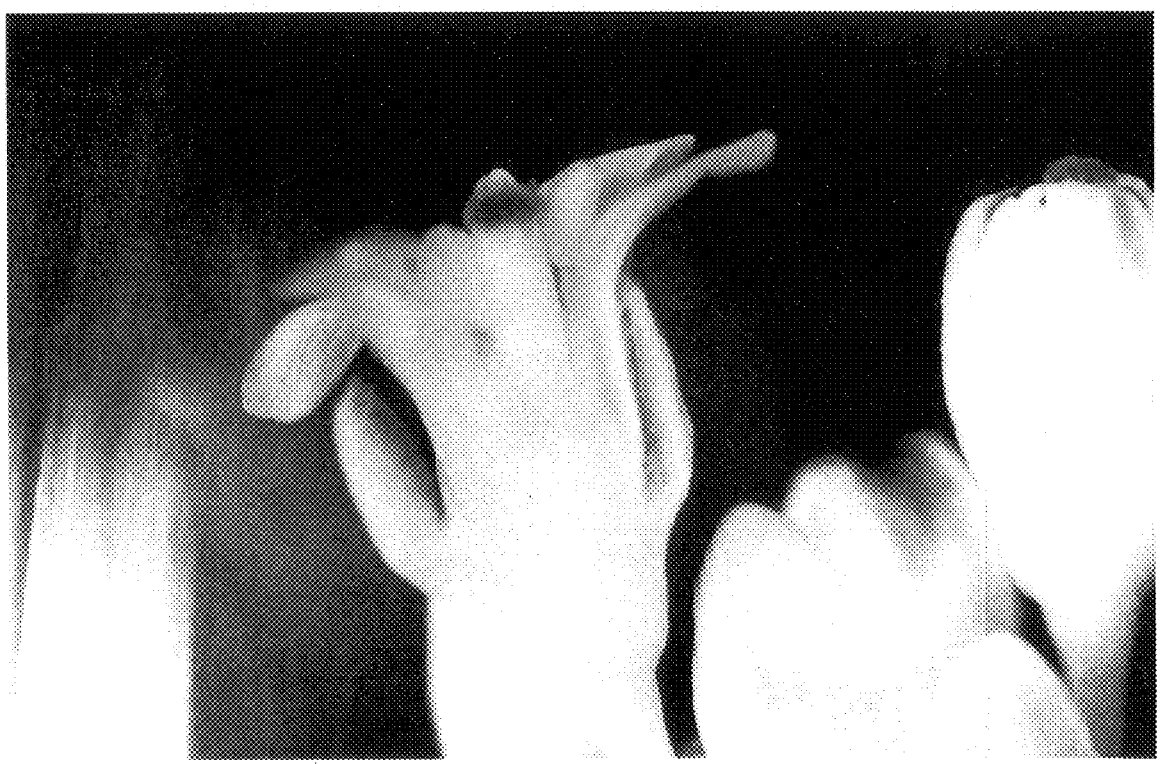
FIGS. 8a and 8b show GUS expression in flowers from *Arobidopsis thaliana* transformed with the binary version of the construct pSilk4-GUS.
Figure 8B:

Transient expression analysis also indicates that the regulatory region obtained from C3 is also active in *Brassica napus* pistils. Furthermore, expression of pSilk4-GUS in transgenic *Arabidopsis thaliana* (FIG. 8) showed that the regulatory region obtained from C3 is also strongly active in the stigma of dicot plants. However expression was also detected in other floral parts (FIG. 8(b)). Therefore, the C3 regulatory region may be used to direct the expression of a gene of interest in pistil, stigma and pollen of dicots and monocors in addition to silk tissues in maize plants. It was also observed, that in transgenic Arabidopsis plants, the C3 regulatory region (pSilk4-GUS) directed the expression of a gene of interest within young leaves, along the margins of mature leaves, and within the stigma and pollen. No expression was observed in roots or in developing fruit. This pattern of expression was also observed in the progeny of these plants.

Deletion constructs for use in the characterization of the regulatory region of C3 are outlined in FIG. 3(b). These constructs comprise a series of 5'deletions of the C3 regulatory region. FIG. 3(b) shows the deletions fragments of the C3 regulatory region, fused with an intron obtained from actin (McElroy, D. et al., 1991. Mol. Gen. Genet. 231: 150–160), GUS, and Nos terminator, however, it is to be understood that these deletion fragments, or other fragments of the C3 regulatory region, may be fused with any gene of interest. Furthermore, any suitable intron may also be used, for example but not limited to, the IVS6 intron from maize (Callis, J., 1987, Genes Dev. 1:

1183–1200). Nucleotides 289–637 of SEQ ID NO's:1 and 2 are homologous to portions of the *Z. mays* Cystathione Synthase gene as well as portions of the Ds element of *Z. mays* transposon Ac. Constructs comprising pSilk7 (comprising nucleotides 732–1986 of SEQ ID NO:2) through to pSilk11, do not contain portions of the Ds element or the cystathione synthase gene.

The silk is also one of the two principal routes of invasion by several pathogens, for example but not limited to, the fungus *Fusarium graminearum*. Fungal spores lodge upon the silk, germinate and the mycelia grow down the strands, either inside or outside, until they reach the ovules where the infection develops further. Preferential expression of pathogen defence genes in silk, using the regulatory region or a fragment thereof, of C3, increases the resistance of corn to Fusarium species. However, it is to be understood that the regulatory region of C3 (SEQ ID NO:2), or a fragment thereof, including but not limited to those outlined in FIG. 3(b), may also be used to regulate gene expression in the pistil of other species, including other monocots as well as dicots.

The regulatory elements of the present invention may also be used in conjunction with other heterologous regulatory elements, such as core promoters, enhancers, or fragments thereof, and the like. For example, the regulatory region or a fragment thereof as defined herein may be used to regulate gene expression of a gene of interest spatially and developmentally within developing silk, pistil, or stigma tissue when combined with a core promoter, for example but not limited to 35S core promoter, the core promoter from T1278 (WO 97/28268), or other core promoters identified above, or as would be known to one of skill in the art. Furthermore, the spatial and developmental regulatory activity of a regulatory element exhibiting silk activity, for example but not limited to, the C3 regulatory region may be further modulated using enhancer elements obtained from either the 35S or T1278 regulatory regions, or other enhancers as would be known to one of skill in the art.

Thus this invention is also directed to regulatory elements obtained from a regulatory element exhibiting silk activity, for example but not limited to, the C3 gene and gene combinations comprising these regulatory regions with other heterologous regulatory elements and genes of interest. Further this invention is directed to such regulatory elements and gene combinations in a cloning vector, wherein the gene is under the control of the regulatory element and is capable of being expressed in a plant cell transformed with the sector. This invention further relates to transformed plant cells and transgenic plants regenerated from such plant cells. The regulatory element, and regulatory element-gene combination of the present invention can be used to transform any plant cell for the production of any transgenic plant. The present invention is not limited to any plant species, or species other than plant.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLE 1
Isolation of Silk Genes

Genes preferentially expressed in silk tissue were isolated by differential screening of corn silk cDNA library with a subtracted corn silk probe and a reverse subtracted seedling probe.

Corn silk cDNA Library constructed using corn silk RNA (extracted with Trizol, Gibco-BRL) and Lambda UNI-ZAP vector (Stratagene). The subtracted corn silk cDNA probe was isolated by subtracting silk cDNA with seedling cDNA using the PCR-Select cDNA Subtraction Kit (Clontech) and labelling with DIG (Boehringer Mannheim). The subtracted probe contained a mixture of cDNA's that are expressed in corn silk tissue but not in seedling tissue. Reverse subtracted seedling cDNA probe was isolated by subtracting seedling cDNA with silk cDNA using the same method as above. The reverse-subtracted probe contains a mixture of cDNA's that are expressed in corn seedling tissue but not in silk tissue.

From this procedure 21 positive clones that hybridize only to the subtracted corn silk probe and not to the reverse-subtracted corn seedling probe were isolated. These putative silk genes were then screened using cDNAs derived from tassel, husk, seedling root, seedling leaf silk or cob cDNA probes by dot blot. From the dot blot screen, 4 clones exhibited silk expression, A1, A3, C1, and C3. These silk genes were sequenced from the 5' and 3' ends and subjected to a Blast search (GenBank) in order to determine homologies. A1, C1 and C3 were found to be the same (C3, SEQ ID NO:3), and encoded a glycine rich protein.

EXAMPLE 2
Northern Analysis: Tissue Specific Expression

The tissue specificity of C3 was confirmed by Northern hybridization using standard techniques. The clones were excised out of the Lambda UNI-ZAP vector as a pBluescript plasmid containing the C3 cDNA insert. The plasmid was used as the template for a DIG-labelled probe.

The DIG-labelled probe was used to hybridize to Total RNA (20 µg/lane) extracted from corn silk, husk, cob, seedling leaf, seedling root, and Brassica leaf (negative control; FIG. 1). These results confirmed that the C3 clone is indeed silk specific. Both probes showed minimal hybridization with corn cob RNA. However, it is highly probable that this is due to trace amounts of silk tissue still attached to kernels of the immature corn cobs.

Northern Analysis: Developmental Expression

Northern analysis was also used to examine the temporal expression of C3 during corn silk development. Corn silk was collected at 0, 2, 4, 6, and 8 days from point of silk emergence (0 day is when corn silk just begins to emerge from the immature cob) and RNA was extracted for hybridization with the C3 probe. 15 µg of total RNA was used per sample (FIG. 2). The hybridization signal decreases with the age of the corn silk, especially in the 4, 6, and 8 day samples. Fertilization of corn silk usually happens within 2 days of silk emergence, and the Northern Blot data indicates that expression of the C3 gene is most active before fertilization.

EXAMPLE 3
Obtaining the Regulatory Region of C3

The regulatory region of the C3 gene was isolated using inverse PCR. Genomic DNA was purified from corn seedlings and digested with the following enzymes: XhoII and NdeI (Separate digestions). These two enzymes were chosen based on the fact that they already cut once within the C3 gene and statistically they are not likely to cut again until 4 Kb upstream and downstream of the gene. The digested genomic DNA fragments were self-circularized under dilute concentrations with T4 DNA ligase and the resulting circularized DNA used as templates in an inverse-PCR reaction. The primer pair c3reverse2 primer (reverse compliment of nucleotides 2096–2120 of SEQ ID NO:1) and c3forward2 primer (nucleotides 2140–2162 of SEQ ID NO:1) were designed approximately 150 bp from the 5' of the C3 cDNA. The primer pair face away from instead of toward each other like in a typical PCR. As a result, the upstream regulatory region was amplified.

The XhoII digested template yielded an approximately 3 KB band while the NdeI digested template yielded an approximately 2 KB band. Both bands were cut from gel slices and cloned into a TA cloning vector (pGEM-T-Easy from Promega.) The resulting clones, pIPCR-XhoII and pIPCR-NdeI were sequenced and the sequences matched each other as well as the original C3 cDNA clone. The pIPCR-XhoII clone contained 2 Kb of regulatory region sequence upstream from the C3 gene while the pIPCR-NdeI clone contained 1.2 Kb of regulatory region sequence. Due to an incomplete partial digest, the pIPCR-XhoI clone contained an additional 0.5 Kb of terminator sequence downstream of the C3 gene.

The position of the transcription start site for the C3 mRNA was determined by primer extension using the Primer Extension procedure described in Short Protocols in Molecular Biology (Ausubel F. M. et al, eds, Wiley and Sons Inc., pp4–20 to 4–22 (1995)) with the following, modifications. The C3-specific extension primer 5'-GAGACCAAAACCACACCAAGCAGAAC-3' (reverse complement of nucleotides 2008–2033 of SED ID NO:1) was radio-labelled with [gamma-32P]ATP and T4 polynucleotide kinase using the protocol supplied by the manufacturer MBI-Fermentas. Unincorporated nucleotides were removed using protocols supplied with the QIAquick Nucleotide Removal kit (Quiagen). The primer extension reaction was performed using Superscript II MMLV-Reverse Transcriptase (Gibco), using two separate amounts of CO272 maize silk total RNA, 10 and 30 µg. The transcription start site was determined, within experimental error, to be at nucleotide 1944 of SED ID NO:1.

The complete 2 KB regulatory region from pIPCR-XhoII was excised and put into a GUS-fusion vector for regulatory activity analysis. The construct was named pSilk1 (FIG. 3(a); nucleotides 1–1959 of SEQ ID NO:1) and contains the regulatory region from 1 to 1959 (excised with AvaII, the closest Restriction Enzyme site upstream from ATG start codon of C3 gene). Another construct, pSilk4 (FIG. 3(a); nucleotides 207–1986 of SEQ ID NO:1) was made in which the regulatory region was amplified using PCR from pIPCR-XhoII. (Primers: ATG primer, reverse compliment of 2096–2120 of SEQ ID NO:1, and c3up2r primer, 207–226 of SEQ ID NO:1). The resulting amplicon contains the regulatory region from 208 to 1987 and contains the complete 5'-untranslated region on the cDNA upstream from the ATG start codon of the C3 gene.

The sequence of the C3 gene was determined (SEQ ID NO:1). The nucleotide sequence of the 5' and 3' noncoding regions of C3 revealed no significant homology to sequences in computer databases. The open reading frame of C3 comprises a glycine-rich domain and exhibits some resemblance to similar domains in glycine-rich proteins. A region containing a small DS-like insertion element (located about 1200 bp upstream of the beginning of the coding region) was also identified.

Constructs comprising fragments of the regulatory region were prepared to characterize the regulatory region. These constructs comprise the IVS6 intron to increase transcriptional stability, and are outlined in FIG. 3(b). Nucleotides 289–637 are homologous to potions of the Z. mays Cystathione Synthase gene as well as portions of the Ds element of Z. mays transposon Ac. pSilk7, comprising nucleotides 888–1986 of SEQ ID NO:2. does not contain the region comprising homology with the Ds element. These 5' deletion fragments of the C3 regulatory region were fused to IVS6 intron, GUS and Nos terminator. These constructs are used for both transient expression assays using particle bombardment, and plant transformation.

EXAMPLE 4
Use of C3 Regulatory Region to Drive Expression of a Gene of Interest

Constructs pSilk1-GUS, pSilk4-GUS, and pSilk7-11-GUS were analysed using particle bombardment followed by assays for GUS expression. pActin-GUS, comprising the regulatory region from Actin, fused with the intron from Actin, and GUS, and the Nos terminator, was used as a positive control.

Three mg of 1.6 um gold particles (Bio-Rad) were coated with 5 ug of DNA in the presence of $CaCl_2$ and spermidine and introduced into corn silk tissue (freshly cut, surface sterilized, and maintained on MS agar), or leaf tissue by micro-projectile particle bombardment (Klein et al 1987 Nature 327:70–73, which is incorporated by reference). The bombarded corn silk, or leaf tissues were assayed for transient GUS expression 12–16 hours )latter. GUS enzymatic activity was detected in the form of blue spots upon addition of X-glue substrate and ferric and ferrous cyanide oxidizers using standard methods.

Both pSilk1 and pSilk4 were active in corn silk, with pSilk4 exhibiting higher GUS expression than the pSilk1 construct (FIG. 4). As a positive control, pActin-GUS (a strong constitutive regulatory element, active in monocot tissues) was also introduced into silk tissue. pActin-GUS activity was 2 to 3 fold higher than GUS activity directed by the pSilk4 construct. A promoter-less GUS construct called pLC.Zprom was used as the negative control and no GUS activity was detected.

The pSilk4-GUS construct was also used to bombard corn leaf tissue (FIG. 5). Low levels of GUS expression were detected, which were much lower than pActin-GUS positive control.

Transient expression assays using particle bombardment were also performed on Brassica napus pistils using pSilk4-GUS construct. GUS expression was detected and indicating that regulatory region of C3 can be useful for pistil specific expression of genes in both monocots and dicots.

Transient expression analysis in corn silk using constructs pSilk7-GUS through pSilk11-GUS (see FIG. 3(b)) was also carried out. Corn silk was prepared and bombarded with these constructs as outlined above. Gus activity was determined 12–16 hours after bombardment. Dark spots indicated expression of GUS within corn silk. Regulatory region activity as observed by the presence or absence of GUS activity is indicated to the right of the constructs in FIG. 3(b). All constructs except pSilk11-GUS showed regulatory region activity. No activity was observed for pSilk11-GUS, suggesting that the nucleotides 1868–1986 of SEQ ID NO:1 are not sufficient by themselves to carry activity in silk tissues. The results also showed that there is a promoter region essential to activity in silk between nucleotides 1668–1868 of SEQ ID NO:1. Deletions between nucleotides 1 and 1668 of SEQ ID NO:1 did not dramatically affect regulatory region activity as assayed by transient assay in silk, since regulatory region activity was maintained.

EXAMPLE 5
Transformation of Arabidopsis and Corn with C3 Regulatory Region

In order to examine the expression of a gene of interest driven by the regulatory region obtained from C3, pSilk4-GUS (FIG. 3(b)) was introduced into corn plants, and Silk4-GUS and pSilk7-GUS was introduced into Arabidopsis plants.

Figure 6A:
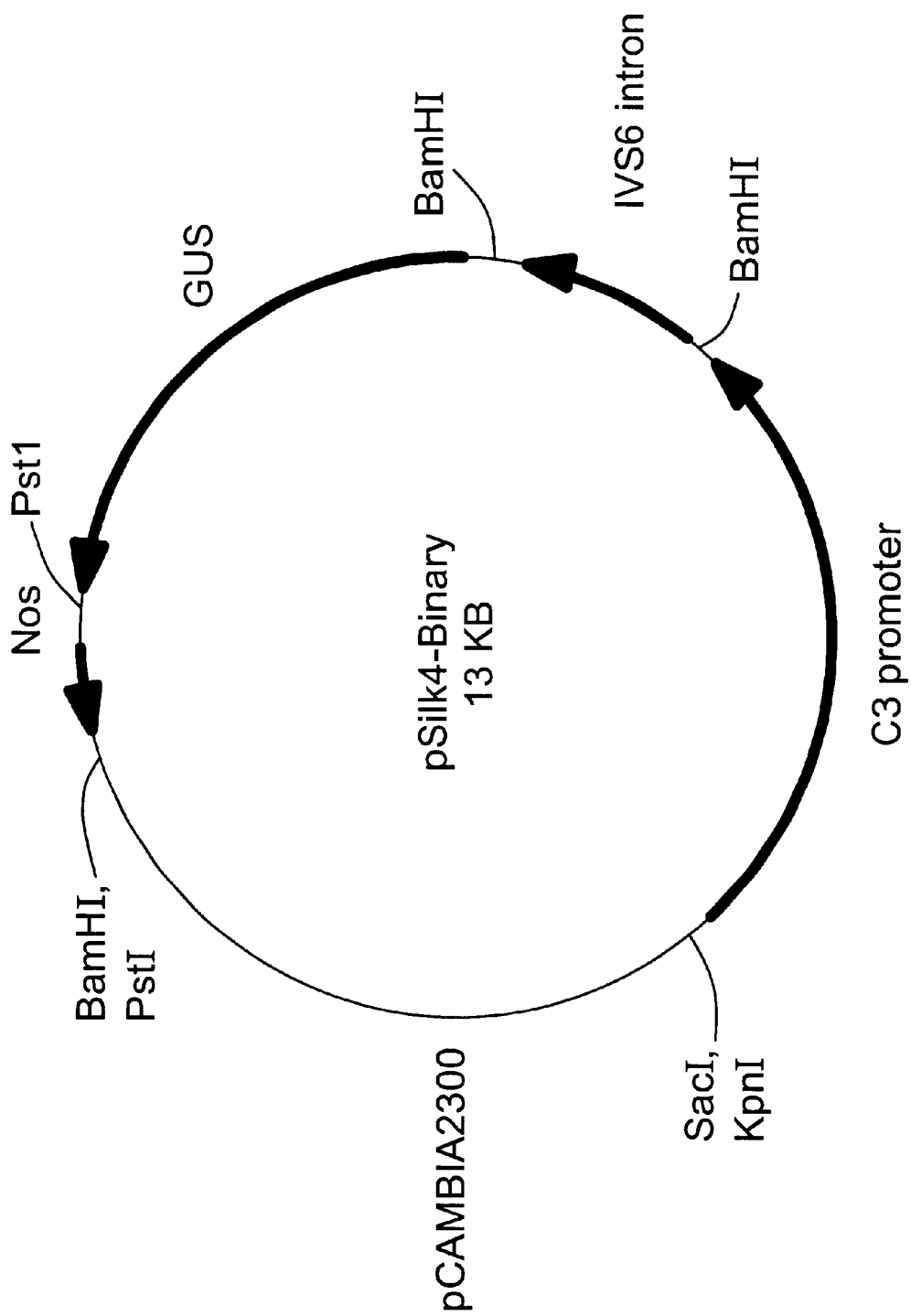
FIGS. 6a and 6b show the diagrammatic representation of the constructs pSILK4 (FIG. 6(a)) and pSILK7 (FIG. 6(b)) in their binary version. The basic vector pCAMBIA 2300 was used for the backbone.
Figure 6B:
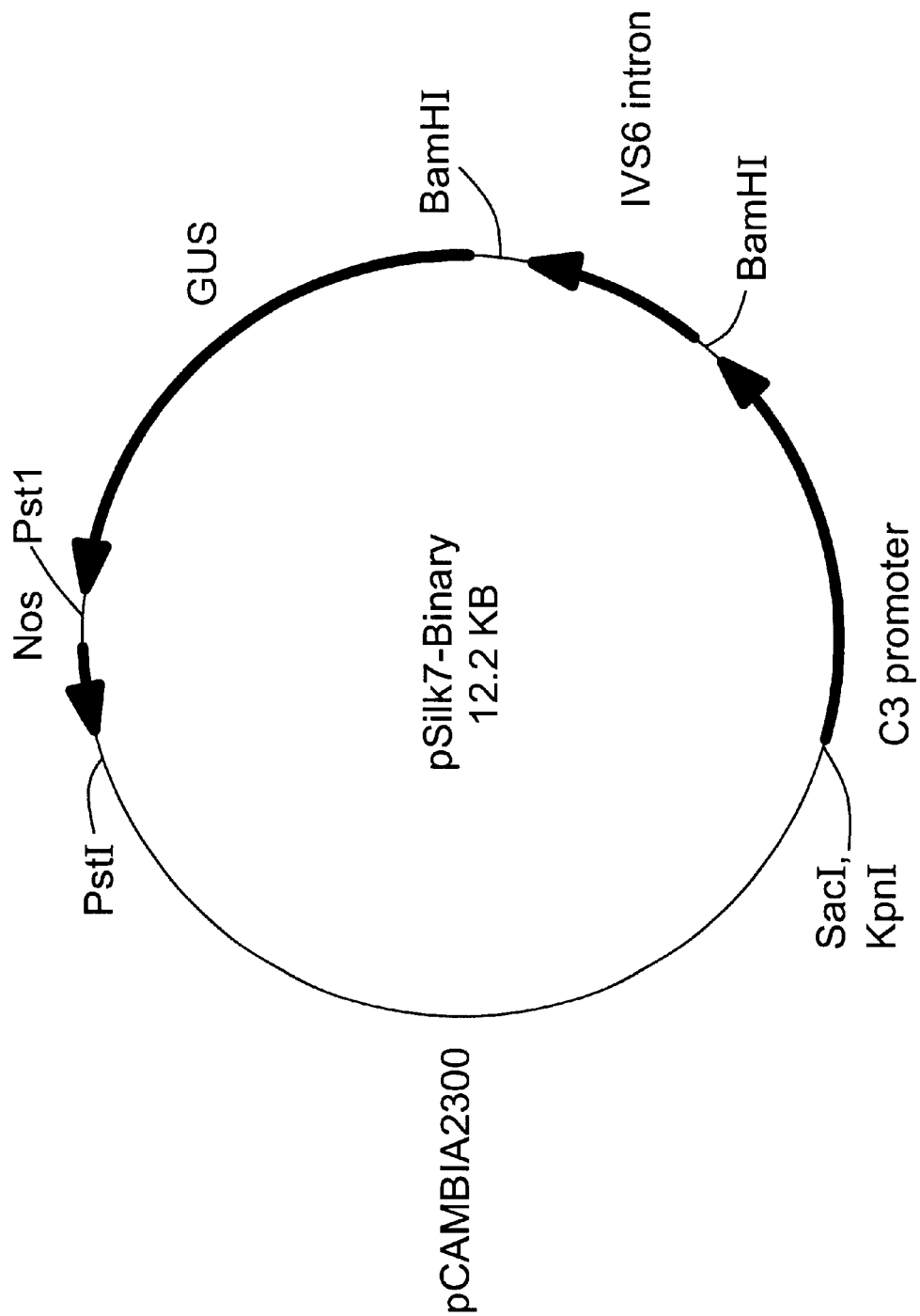

Constructs pSilk4-Binary-GUS and pSilk7-Binary-GUS (FIG. 6(a) and (b), respectively) were prepared using pCAMBIA2300. These constructs were introduced into Agrobacterium rumefaciens for Arabidopsis transformation. Vector pSilk4-GUS (FIG. 3(b)) was used for corn transformation.

Z. mays plants were transformed via bombardment, essentially following the protocol of Morrish et al. (1990, Biotechnology 8:833–939; which is incorporated by reference). Arabidopsis plants were transformed using Agrobacterium following the leaf dip protocol of Clough and Bent (1998, Plant J. 16:735–743, which is incorporated by reference).

Corn tissues were examined for the occurrence of the introduced transgenes using PCR analysis. Plants comprising the transgenes were assayed for GUS activity in silk, leaf, husk, tassel and pollen tissues (see Table 1).

TABLE 1

GUS activity in maize lines transformed with pSilk4-GUS

| Plant No. | GUS Expression | | | |
|---|---|---|---|---|
| | Leaf | Silk | Tassel** | Pollen |
| negative transfomants* | — | — | endogenous | — |
| 7a-1-2 | — | ✓ | endogenous | nd |
| 7b-2-1 | — | — | endogenous | ✓ |
| 7b-3-5 | — | — | endogenous | ✓ |
| 7b 12-1 | — | ✓ | endogenous | nd |

Figure 7A:
FIGS. 7a and 7b show GUS expression in silk strands from corn transformed with the construct pSilk4-GUS. The C3 regulatory region was fused to GUS and used for stable transformation of corn using particle bombardment. GUS activity was detected by histological staining.

✓, presence of GUS activity;
—, absence of GUS activity;
*plants were negative for presence of construct as determined by PCR;
**tassels contain an endogenous level of GUS activity in non-transformants;
nd, not determined Corn transgenic lines comprising pSilk4-GUS were recovered that exhibited GUS activity in silk strands (FIG. 7(a)). Activity was also detected in pollen rains. No GUS activity was detected in leaf, cob and tassel tissues.

Figure 7B:
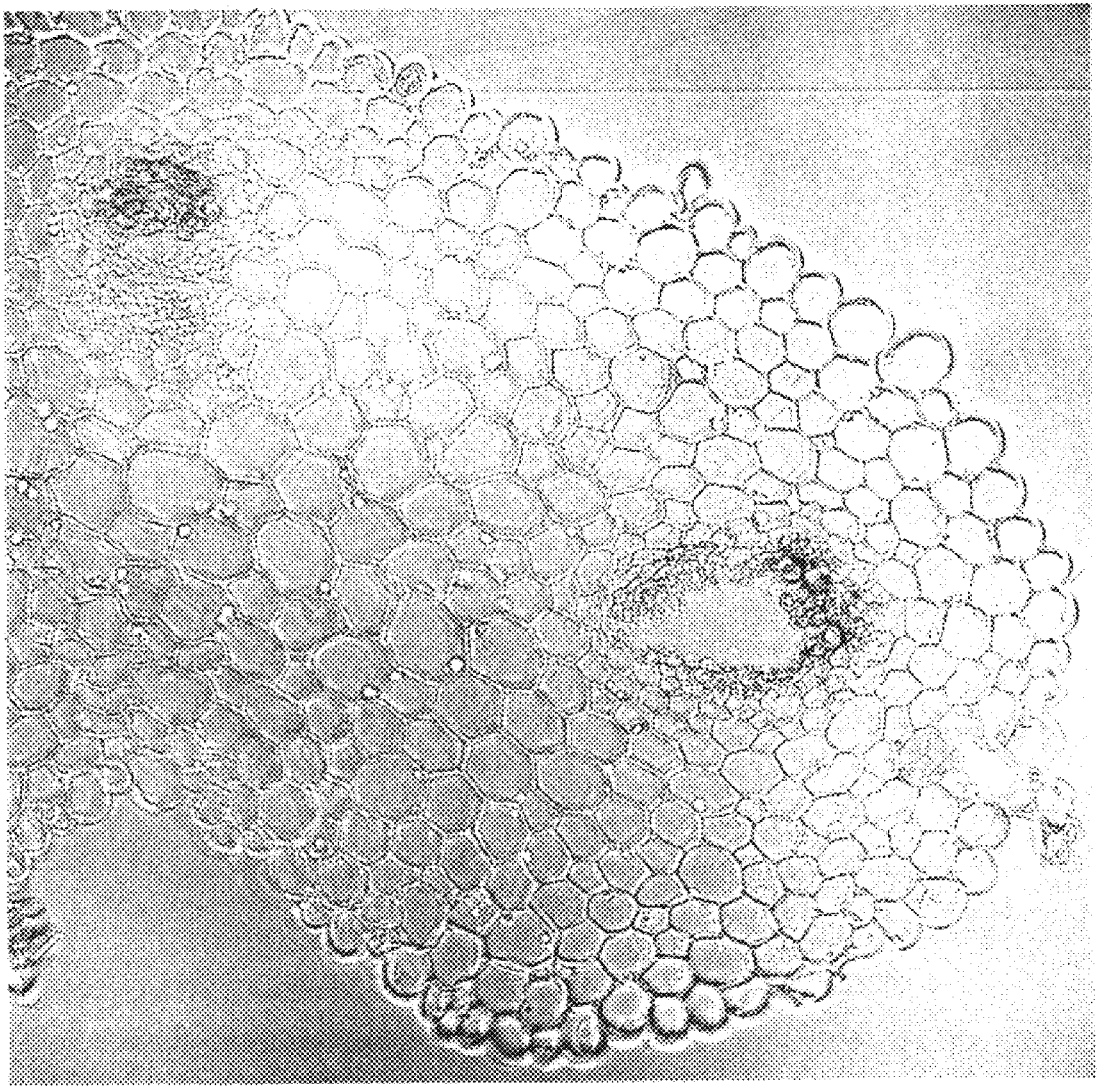

Some of the GUS positive silk strands were processed for cryosection following GUS detection. Briefly, strands were transferred to the fixing solution (5% formaldehyde, 5% glacial acetic acid, 20% Ethanol), followed by a series of transfers to ethanol solutions to dehydrate and preserve the tissues (50% Ethanol, 75% Ethanol, 100% Ethanol) then rehydrate for cryo-sectioning (90% Ethanol, 80%, 70%, 60%, 50% Ethanol, 25% Ethanol), and a final transfer in PBS where sucrose was added to final 30% as a cryoprotectant, let dissolved at 4 C. for 2 days. Tissue in 30% sucrose were ready for cryo-sectioning. Segments of silk were then frozen in TissueTek O.C.T. compound (Miles Inc., Elkart Ind.) and 10 μm sections were cut using a Reichert-Jung Cryocut E microtome (Reichert, Vienna). Sections were transferred to class slides that were pre-treated with Fro-Tissuer Pen (Electron Microscopy Sciences, Fort Washington, Pa.) and allowed to dry overnight. Sections were counterstained briefly in 0.5% Safranin O (aqueous) for microscopy. GUS activity was specifically located in the area of the vascular bundles, including the companion cells (FIG. 7(b)).

Tissues from Arabidopsis plants transformed with either pSilk4-Binary-GUS or pSilk7-Binary-GUS were assayed for GUS activity in complete seedling, young and mature leaves, whole flowers and developing fruits. Strong activity in the stigmas of the flowers was consistently observed in plants transformed with pSilk4-Binary-GUS construct. Stigma specific expression lines were generated (FIG. 8(a)). In addition, some transgenic lines exhibited various level of expression in other tissues, including pistil, sepal, petal, anther and pollen (see one example in FIG. 8(b)). Preliminary analysis of plants transformed with the pSilk7-Binary-GUS construct showed similar type of expression patterns. This suggested that the nucleotides 208 to 888 of SEQ ID NO:1, which include a portion of a DS element and a truncated cystathione synthase gene, are not needed for the C3 promoter activity in plants. In several Arabidopsis plants, pSilk4-GUS activity was observed in young leaves, along the margins of mature leaves, and within the stigma and pollen. No expression was observed in roots or in developing fruit. This pattern of expression was also observed in the progeny of these plants.

The pSilk4 regulatory region was also used to drive silk expression of a modified RPL3 gene, termed RPLC4 (WO 99/09173, which is incorporated herein by reference; RPLC4 was obtained from Linda Harris: Eastern Cereal Oilseed Research Centre, Agriculture and AgriFood Canada, Ottawa). Constructs comprising pSilk4-RPLC4 with the actin intron (McElroy, D., et al., Wu, R. 1991. Mol. Gen. Genet. 231: 150–160; FIG. 3(c)) were used to transform corn plants using the above protocol.

Plants expressing pSilk4-RPLC4 exhibit resistance to Fusarium infection as shown in field inoculation experiments. Briefly, plants were inoculated by injecting a suspension of *Fusarium graminearum* spores in their silk channels 4 to 6 days after silk emergence. Plants were maintained in a humid environment for a few weeks. Visual evaluation of disease on ears was done about 2 months after inoculation. Level of the Fusarium mycotoxin DON was also measured using a specific antibody.

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Atkinson, A. H., Heath, R. L., Simpson, R. J., Clarke, A. E., Anderson, M. A. 1993. Plant Cell 5, 203–213.

Bonnett, O. T. 1948. Ear and tassel development in maize. Annals of the Missouri Botanical Garden 35, 269–287.

Callis, J., Fromm, M., Walbot, V. 1987. Introns increase gene expression in cultured maize cells. Genes Dev. 1: 1183–1200.

Cheng, S. H., Keller, B., Condit, C. M. 1996. Common occurrence of homologues of petunia glycine-rich protein-1 among plants. Plant Mol. Biol. 31, 163–168.

Condit, C. M. 1993. Developmental expression and localization of petunia glycine-rich protein 1. Plant Cell 5, 277–288.

De Oliveira, D. E., Franco, L. O., Simoens, C., Seurinck, J., Coppoeters, J., Botterman, J., Van Montagu, M. 1993. Inflorescence-specific genes from *Arabidopsis thaliana* encoding glycine-rich proteins. Plant J. 3, 495–507.

Dzelzalns, V. A., Thorsness, M. K., Dwyer, K. G., Baxter, J. S., Balent, M. A., Nasrallah, M. E., Nasrallah, J. B. 1993. Distinct cis-acting elements direct pistil-specific and pollen-specific activity of the Brassica S locus glycoprotein gene promoter. Plant Cell 5, 855–863.

Goddemeier, M. L., Wulff, D., Feix, G. 1998. Root-specific expression of a *Zea mays* gene encoding a novel glycine-rich protein, zmGRP3. Plant Mol. Biol. 36, 799–802.

Goring, D. R., Glavin, T. L., Schafer, U., Rothstein, S. J. 1993. Plant Cell 5, 531–539.

Heslop-Harrison, Y., Reger, B. J., Heslop-Harrison, J. 1984. The pollen-stigma interaction in the grasses. Tissue organisation and cytochemistry of the stigma ("silk") of *Zea mays* L. Acta Bot. Neerl. 33, 81–99.

Hirose, T., Sugita, M., Sugiura, M. 1993. CDNA structure, expression and nucleic acid-binding properties of three RNA-binding proteins in tobacco: occurrence of tissue-specific alternative splicing. Nucleic Acids Res. 21, 3981–3987.

Lei, M., Wu, R. 1991. A novel glycine-rich cell wall protein gene in rice. Plant Mol Biol. 16, 17–198.

Leung, D. W. M. 1992. Phytochemistry 313, 1899–1900.

Ludevid, M. D., Freire, M. A., Gomez, I., Burd. C. G., Albericio, F., Giralt, E., Dreyfuss, G., Pages, M. 1992. RNA binding characteristics of a 16 kDa glycine-rich protein from maize. Plant J. 2, 999–1003.

McElroy, D., Blowers, a., Jenes, B., Wu, R. 1991. Construction of expression vectors based on the rice actin 1 (Act1) 5'region for use in monocot transformation. Mol. Gen. Genet. 231: 150–160.

Mirabella, R., Martirani, L., Lambert, A., Iaccarino, M., Chiurazzi, M. The soybean ENOD40(2) promoter is active in *Arabidopsis thaliana* and is temporally and spatially regulated. Plant Mol Biol. 39, 177–181.

Morrish, F., Armstrong, C., Williams, R., Thomas, J., Klein, T. M. 1990. Inheritance and expression of chimericgenes in the progeny of transgenic maize plants. Biotechnolgy. 8, 833–839.

Nasrallah, J. B., Nasrallah, M. E. 1993. Plant cell 5, 1325–1335.

Nicolas, C., Rodriguez, D., Poulsen, F., Eriksen, F. N., Nicolas, G. 1997. The expression of an absicisic acid-responsive glycine-rich protein coincides with the level of seed dormancy in *Fagus sylvatica*. Plant Cell Physiol. 38, 1303–1310.

Parsons, B. L., Mattoo, A. K. 1994. A wound-repressible glycine-rich protein transcript is enriched in vascular bundles of tomato fruit and stem. Plant Cell Physiol. 35, 27–35.

Quigley, F., Villiot, M. L., Mache, R. 1991. Nucleocide sequence and expression of a novel glycine-rich protein gene from *Arabidopsis thaliana*. Plant Mol. Biol. 17, 949–952.

Ryser, U., Schorderet, M., Zhao, G. F., Studer, D., Ruel, K., Hauf, G., Keller, B. Structural cell-wall proteins in protozylem development: evidence for a repair process mediated by a glycine-rich protein. Plant J. 12, 97–111.

Satuka, C., Oda, A., Yamakawa, S., Satoh, S. 1998. Root-specific expression of genes for novel glycine-rich proteins cloned by use of an antiserum against xylem sap proteins of cucumber. Plant Cell Physiol. 39, 1330–1336.

Trick, M., Heizmann, P. 1992. Int. Rev. Cytol. 140, 485–524.

Yasuda, E., Ebinuma, H., Wabiko, H. 1997. A novel glycine-rich/hydrophobic 16 kDa polypeptide gene from tobacco: similarity to proline-rich protein genes and its wound-inducible and developmentally regulated expression. Plant Mol Biol. 33, 667–678.

The embodiments of the invention in which an exclusive property of privilege is claimed are defined as follows:

1. An isolated nucleic acid that hybridizes under stringent conditions with a nucleotide sequence or a complement thereof selected from the group consisting of:
   nucleotides 1 to about 1668 of SEQ ID NO:2
   nucleotides 1 to about 1986 of SEQ ID NO:2
   nucleotides 1 to about 1959 of SEQ ID NO:2;
   nucleotides about 208 to about 1986 of SEQ ID NO:2;
   nucleotides about 888 to about 1986 of SEQ ID NO:2;
   nucleotides about 1134 to about 1986 of SEQ ID NO:2;
   nucleotides about 1446 to about 1986 of SEQ ID NO:2;
   nucleotides about 1668 to about 1986 of SEQ ID NO:2;
   nucleotides about 1868 to about 1986 of SEQ ID NO:2; and
   nucleotides about 1668 to about 1868 of SEQ ID NO:2,
wherein said stringent conditions comprise hybridizing said nucleic acid to said nucleotide sequence in 4×SSC at 65° C. followed by washing in 0.1×SSC at 65° C. for an hour, wherein said isolated nucleic acid exhibits silk activity.

2. The isolated nucleic acid of claim 1 comprising nucleotides 1 to about 1959 of SEQ ID NO:2.

3. The isolated nucleic acid of claim 1 comprising nucleotides from about 208 to about 1986 of SEQ ID NO:2.

4. The isolated nucleic acid of claim 1 comprising nucleotides from about 888 to about 1986 of SEQ ID NO:2.

5. The isolated nucleic acid of claim 1 comprising nucleotides from about 1134 to about 1986 of SEQ ID NO:2.

6. The isolated nucleic acid of claim 1 comprising nucleotides from about 1442 to about 1986 of SEQ ID NO:2.

7. The isolated nucleic acid of claim 1 comprising nucleotides from about 1668 to about 1986 of SEQ ID NO:2.

8. The isolated nucleic acid of claim 1 comprising nucleotides from about 1668 to about 1868 of SEQ ID NO:2.

9. The isolated nucleic acid of claim 1 comprising nucleotides 1 to about 1986 of SEQ ID NO:2.

10. The isolated nucleic acid of claim 1 comprising nucleotides 1 to about 1668 of SEQ ID NO:2.

11. A chimeric construct comprising the nucleic acid of claim 1 in operative association with a coding sequence of interest.

12. The chimeric construct of claim 11 further comprising a heterologous regulatory element in operative association with said nucleic acid and said coding sequence of interest.

13. A vector comprising the chimeric construct of claim 11.

14. The chimeric gene construct of claim 11 wherein said nucleic acid comprises nucleotides from about 208 to about 1986 of SEQ ID NO:2 in operative association with RPLC4.

15. A vector comprising the chimeric construct of claim 12.

16. A transgenic plant cell comprising the vector of claim 13.

17. A transgenic seed comprising the vector of claim 13.

18. A transgenic plant comprising the vector of claim 13.

19. A method of producing a plant expressing a coding sequence of interest within silk or pistil tissue comprising:
  i) transforming a plant with a vector of claim 13 to produce a transformed plant; and
  ii) growing said transformed plant.

20. The chimeric construct of claim 14, further comprising an intron in operative association with said nucleic acid.

21. A transgenic plant cell comprising vector of claim 15.

22. A transgenic seed comprising the vector of claim 15.

23. A transgenic plant comprising the vector of claim 15.

24. The method of claim 19, wherein the step of transforming further comprises as step of confirming the presence of said coding sequence in said transformed plant.

* * * * *